United States Patent
Zhang et al.

(10) Patent No.: US 12,097,194 B2
(45) Date of Patent: Sep. 24, 2024

(54) COMBINATION THERAPY FOR TREATING BLOOD CANCER

(71) Applicant: SIGNALCHEM LIFESCIENCES CORPORATION, Richmond (CA)

(72) Inventors: Zaihui Zhang, Richmond (CA); Xiaoyan Jiang, Richmond (CA); Katharina Rothe, Richmond (CA); Xiaojia Niu, Richmond (CA)

(73) Assignee: SIGNALCHEM LIFESCIENCES CORPORATION, Richmond (CA)

( * ) Notice: Subject to any disclaimer, the term of this patent is extended or adjusted under 35 U.S.C. 154(b) by 736 days.

(21) Appl. No.: 17/276,459

(22) PCT Filed: Sep. 18, 2019

(86) PCT No.: PCT/US2019/051764
§ 371 (c)(1),
(2) Date: Mar. 15, 2021

(87) PCT Pub. No.: WO2020/061216
PCT Pub. Date: Mar. 26, 2020

(65) Prior Publication Data
US 2022/0031685 A1 Feb. 3, 2022

Related U.S. Application Data

(60) Provisional application No. 62/732,816, filed on Sep. 18, 2018.

(51) Int. Cl.
*A61K 31/4545* (2006.01)
*A61K 31/635* (2006.01)
*A61P 35/02* (2006.01)

(52) U.S. Cl.
CPC ........ *A61K 31/4545* (2013.01); *A61K 31/635* (2013.01); *A61P 35/02* (2018.01)

(58) Field of Classification Search
CPC .... A61K 31/4545; A61K 31/635; A61P 35/02
See application file for complete search history.

(56) References Cited

U.S. PATENT DOCUMENTS 7,390,799 B2   6/2008  Bruncko et al.
7,973,161 B2 *  7/2011  Bruncko .............. C07D 335/02
                                                                544/393

(Continued)

FOREIGN PATENT DOCUMENTS

JP    2008-540577 A    11/2008
JP    2017-501981 A    1/2017

(Continued)

OTHER PUBLICATIONS

Sharma, P., Pollyea, D.A. Shutting Down Acute Myeloid Leukemia and Myelodysplastic Syndrome with BCL-2 Family Protein Inhibition. Curr Hematol Malig Rep 13, 256-264 (2018) (Year: 2018).*

(Continued)

*Primary Examiner* — Clinton A Brooks
*Assistant Examiner* — Jerica Katlynn Wilson
(74) *Attorney, Agent, or Firm* — Seed IP Law Group LLP

(57) ABSTRACT

Provided herein are combination therapies for treating blood cancer, in particular, acute myeloid leukemia, by concurrently targeting Axl and BCL-2.

12 Claims, 10 Drawing Sheets

(56) References Cited

U.S. PATENT DOCUMENTS 9,345,702 B2     5/2016   Elmore et al.
2017/0022189 A1   1/2017   Zhang

FOREIGN PATENT DOCUMENTS

| WO | 2007/040650 A2 | 4/2007 | |
|---|---|---|---|
| WO | 2010/083465 A1 | 7/2010 | |
| WO | 2014/020043 A1 | 2/2014 | |
| WO | WO-2015081257 A2 * | 6/2015 | ......... A61K 31/4427 |

OTHER PUBLICATIONS

Palmer et al. Combination cancer therapy can confer benefit via patient-to-patient variability without drug additivity or synergy Cell. Dec. 14, 2017; 171(7): 1678-1691 (Year: 2017).*

Hong et al., "Receptor tyrosine kinase AXL is induced by chemotherapy drugs and overexpression of AXL confers drug resistance in acute myeloid leukemia," *Cancer Letters* 268:314-324, Sep. 18, 2008. (11 pages).

International Search Report and Written Opinion, dated Nov. 27, 2019, for International Application No. PCT/US2019/051764. (9 pages).

Pan et al., "Selective BCL-2 Inhibition by ABT-199 Causes On-Target Cell Death in Acute Myeloid Leukemia," *Cancer Discovery* 4:362-375, Mar. 2014 [Published online Dec. 17, 2013]. (15 pages).

* cited by examiner

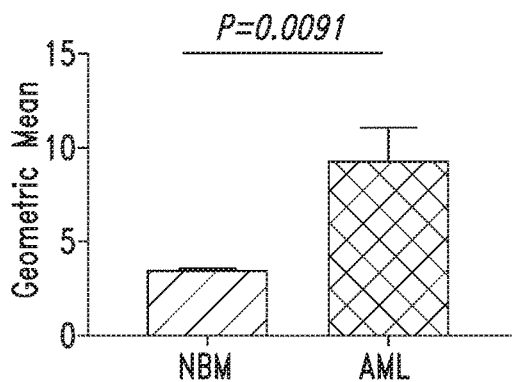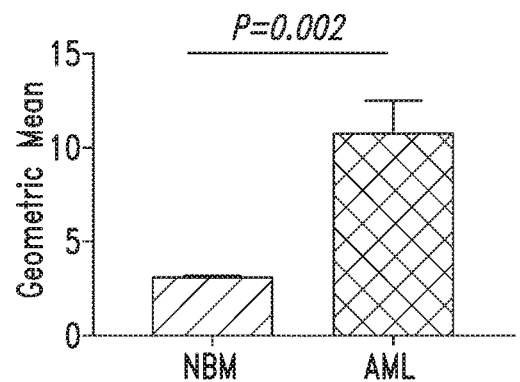
*FIG. 2A*  *FIG. 2B*

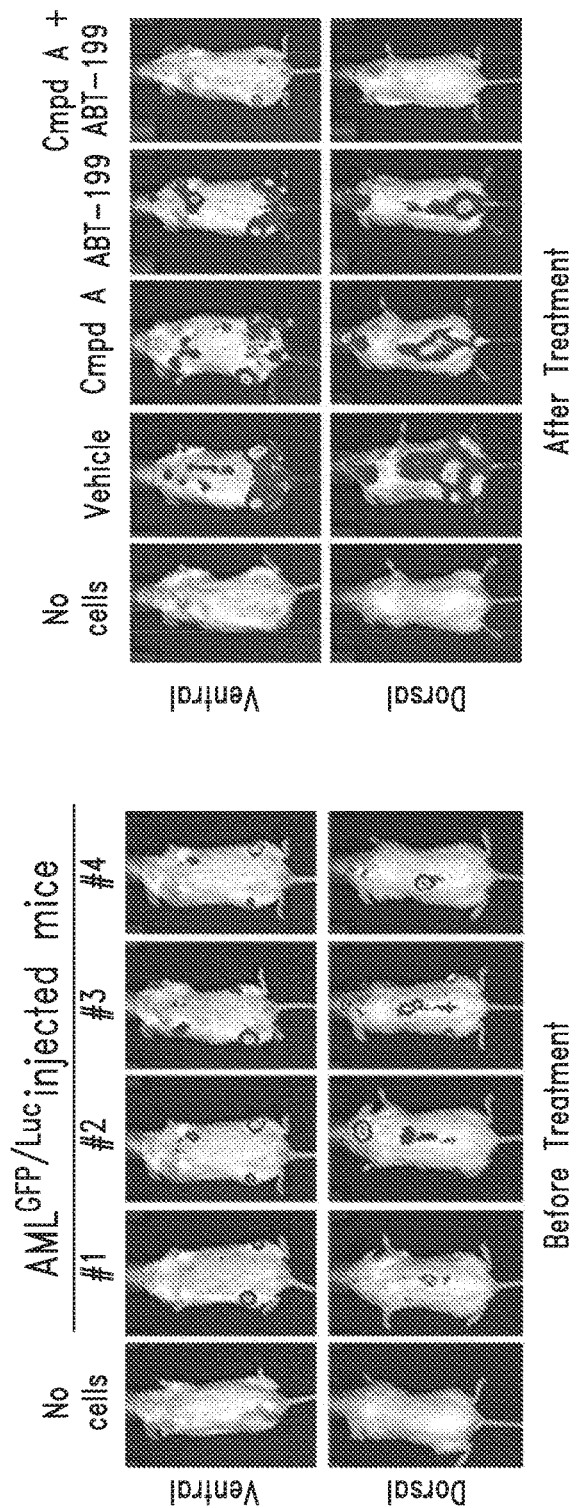
FIG. 4A
FIG. 4B
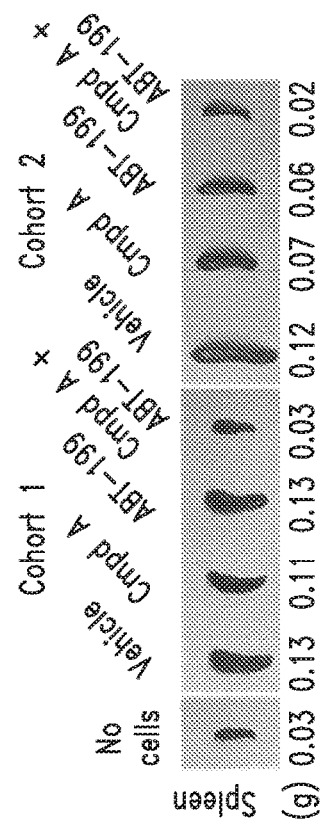
FIG. 5

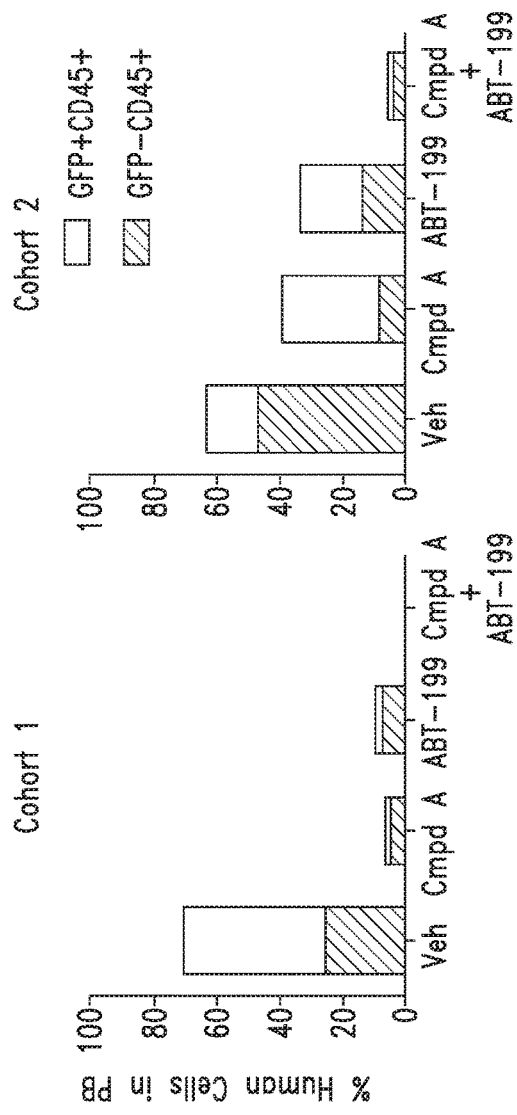
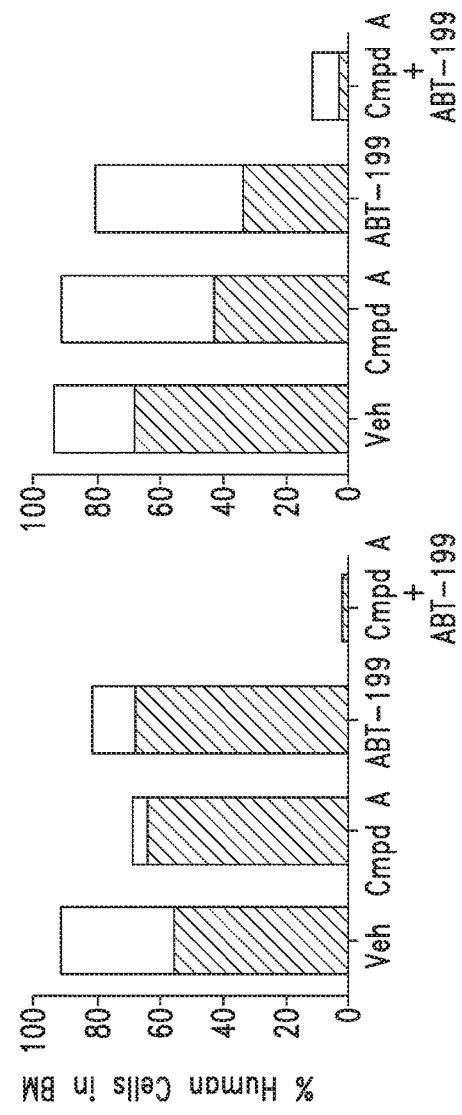
FIG. 6A  FIG. 6B  FIG. 6C  FIG. 6D

COMBINATION THERAPY FOR TREATING BLOOD CANCER

CROSS-REFERENCE TO RELATED APPLICATIONS

This application claims the benefit under 35 U.S.C. § 119(e) of U.S. Provisional Patent Application No. 62/732,816 filed Sep. 18, 2018 which application is incorporated herein by reference in its entirety.

BACKGROUND

Technical Field

The present disclosure provides a combination therapy for treating blood cancer, in particular, acute myeloid leukemia.

Description of the Related Art

Acute myeloid leukemia (AML) is characterized by clonal expansion of leukemic stem cells (LSCs) and myeloid precursors (blasts), resulting in impaired hematopoiesis and bone marrow (BM) failure (1-3). It is highly heterogeneous, with up to nine individual categories of genetic alterations (1,2,4-6). Although major progress has recently been made in identifying molecular and genetic subgroups, AML therapies and long-term patient outcomes have not improved significantly over the past 40 years (3,4,7). The 5-year survival rate thus remains at less than 40% for patients <60 years and only 10-20% for older patients (1,8). While standard induction chemotherapies, such as anthracycline or cytoarabine, lead to an initial reduction in myeloid blast cells in most patients, none of the currently available treatments are curative. Drug resistance and relapse remain major causes for treatment failure, highlighting the need for more effective therapies (9-11). In addition, it has been demonstrated that LSCs and their progenitors from human blood cancers are highly resistant to current therapies, which maintain the potential for relapse in many patients (12-17). Thus, improved therapies are urgently needed for AML.

SUMMARY OF THE INVENTION

The present disclosure is related to combination therapies that provide superior therapeutic outcome to that of the currently available therapies. Various embodiments are directed to methods for treating blood cancer (e.g., AML) in a subject in need thereof, the method comprising administering to the subject at least one TAM family kinase inhibitor (e.g., an Axl inhibitor) in combination with at least one BCL-2 family protein inhibitor. Advantageously, the combination therapies disclosed herein are demonstrated to provide more than additive potency and synergistic therapeutic effects compared to monotherapies administered separately.

In one embodiment, the TAM family kinase inhibitor utilized in the combination therapies is a potent Axl inhibitor.

In more specific embodiments, the Axl inhibitor is a compound of Formula (I):

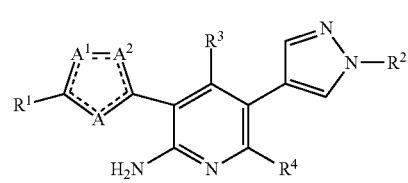

Formula (I)

wherein,
A, $A^1$ and $A^2$ is the same or different and independently —N=, —$CR^5$=, or —O—;

$R^1$ is alkyl, cycloalkyl, cycloalkylalkyl, haloalkyl, aryl, aralkyl, heterocyclyl, heterocyclylalkyl, heteroaryl, or heteroarylalkyl, each of which may be optionally substituted;

$R^2$ is heterocyclyl, heterocyclylalkyl, cycloalkyl, alkyl, aralkyl, cycloalkylalkyl, heteroaryl, heteroarylalkyl, or aryl, each of which may be optionally substituted;

each $R^3$ and $R^4$ is the same or different and independently selected from hydrogen, alkyl, aralkyl, alkenyl, aralkenyl, alkynyl, aralkynyl, cycloalkyl, cycloalkylalkyl, halo, or haloalkyl, each of which may be optionally substituted;

$R^5$, at each occurrence, is hydrogen, alkyl, aralkyl, cycloalkyl, cycloalkylalkyl, halo, or haloalkyl, each of which may be optionally substituted; or a stereoisomer, enantiomer or tautomer thereof, a pharmaceutically acceptable salt thereof, or a pharmaceutical composition thereof.

In a preferred embodiment, the Axl inhibitor is 3-(5-(cyclopropylmethyl)-1,3,4-oxadiazol-2-yl)-5-(1-(piperidin-4-yl)-1H-pyrazol-4-yl)pyridin-2-amine (Compound A):

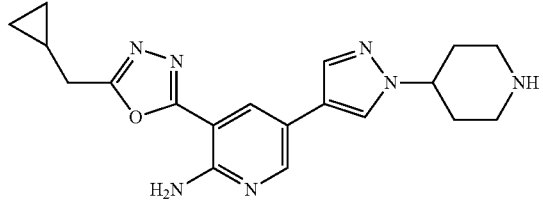

Compound A

In another embodiment, the BCL-2 family protein inhibitor is a compound of Formula (II):

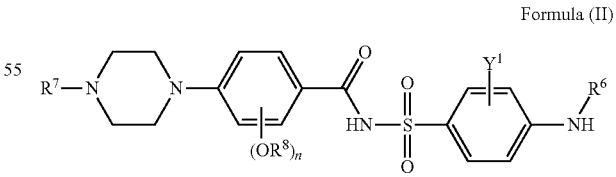

Formula (II)

wherein
n is 0 or 1;
$R^6$ is optionally substituted heterocyclylalkyl, optionally substituted cycloalkylalkyl or optionally substituted heteroalkyl;
$R^7$ is optionally substituted heterocyclylalkyl;

R[8] is optionally substituted heteroaryl or optionally substituted aryl;

Y[1] is an electron-withdrawing group.

In more specific embodiments, the BCL-2 inhibitor is Venetoclax (VENCLEXTA®, also known as ABT-199), or Navitoclax (also known as ABT-263):

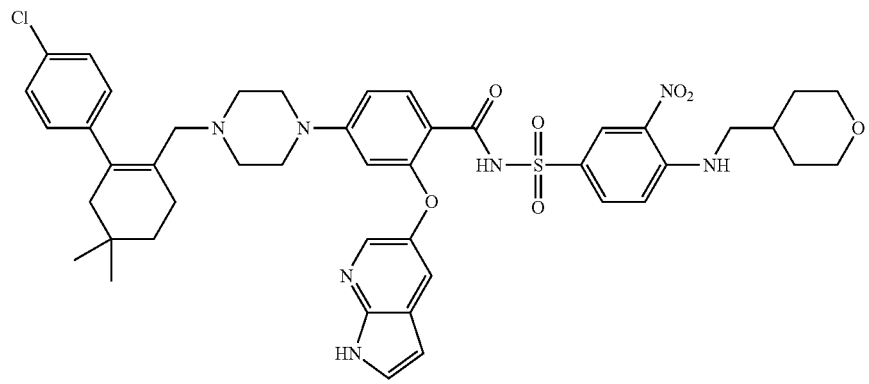

Venetoclax (VENCLEXTA®)

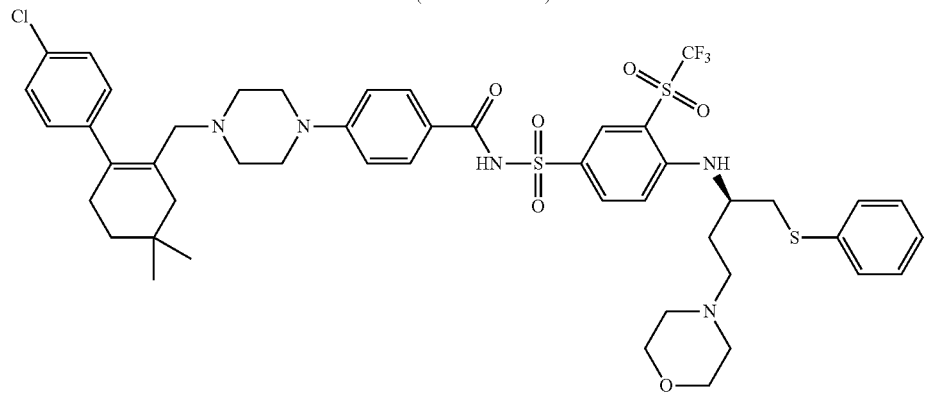

Navitoclax

In more specific embodiments, the combination therapy comprises concomitant administration of an Axl inhibitor and a BCL-2 family protein inhibitor for treating blood cancer, including for example, leukemia, lymphoma or myeloma. In more specific embodiments, the blood cancer is AML.

A further embodiment provides in vivo assay capable of determining the effectiveness of a compound of Formula (I) in combination with one or more chemotherapeutic agents in preventing, treating or managing blood cancer, e.g., AML, in a patient.

BRIEF DESCRIPTION OF THE FIGURES

FIG. 2A and FIG. 2B show cell surface expression of Axl for AML patient samples and normal bone marrow (NBM) donor cells for CD34+ AML and stem-enriched CD34+ CD38− AML respectively.

FIG. 4A and FIG. 4B show bioluminescent images of mice from a patient-derived xenograft (PDX) model of AML before treatment (FIG. 4A) and after treatment (FIG. 4B) with Axl inhibitor monotherapy, BCL-2 inhibitor monotherapy and Axl/BCL-2 inhibitor combination therapy.

FIG. 5 shows spleen sizes and weights of representative euthanized mice from a PDX model of AML from each treatment group as indicated for each patient cohort.

FIG. 6A and FIG. 6B show fluorescence-activated cell sorting (FACS) analysis of engraftment of transduced (GFP+) and untransduced (GFP−) human leukemic cells in peripheral blood (PB) of representative euthanized mice from each treatment group in a PDX model of AML.

FIG. 6C and FIG. 6D show fluorescence-activated cell sorting (FACS) analysis of engraftment of transduced (GFP+) and untransduced (GFP−) human leukemic cells in bone marrow (BM) of representative euthanized mice from each treatment group in a PDX model of AML

DETAILED DESCRIPTION

Figures 1A, 1B:
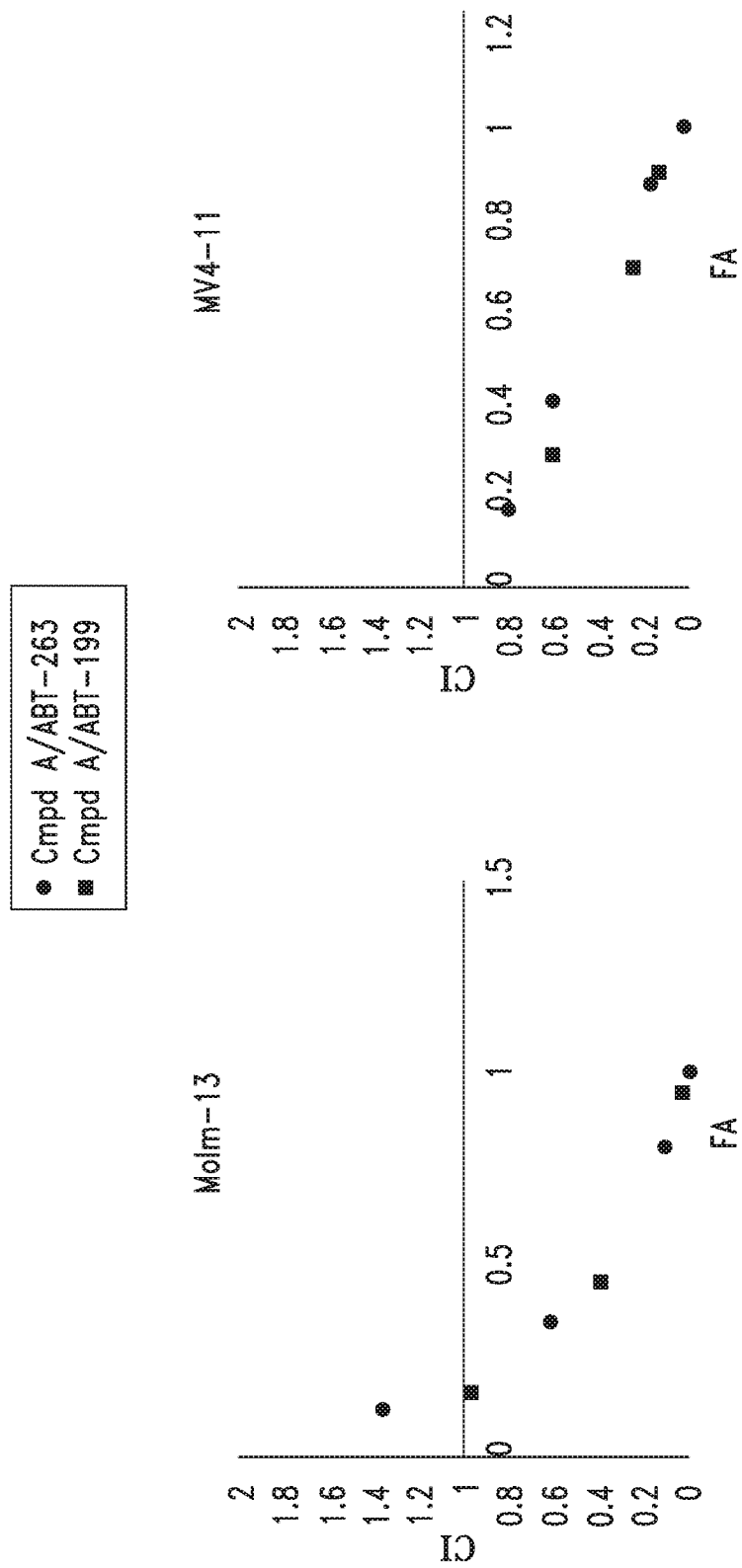
FIG. 1A and FIG. 1B show the combination index values for Axl/BCL-2 inhibitor combination therapies against the Molm-13 and MV4-11 AML cell lines, respectively.

Various embodiments of the present disclosure are directed to combination therapies utilizing a TAM family kinase inhibitor (e.g., an Axl inhibitor) in combination with a BCL-2 family protein inhibitor for treating blood cancer, in particular, acute myeloid leukemia (AML).

Synergistic Effects of Targeting Axl and BCL-2

GAS6/Axl signaling is critical in the pathogenesis of AML and therapy resistance. One candidate target for the treatment of AML is Axl, a member of the TAM (TRYO3, Axl and MER) family of receptor tyrosine kinases (18,19). There are four putative TAMR ligands: growth arrest-specific gene 6 (GAS6), Protein S, TUBBY and TUBBY like protein 1 (TULP1) (18,20). Interestingly, GAS6 has sub-nanomolar affinity for Axl and is the only activating ligand for Axl. TAMR is overexpressed in many solid tumors and enhances survival and resistance to apoptosis (18,19). Axl plays a critical role in mediating migration and invasiveness of cancer cells. Particularly, Axl and GAS6 expression have been reported to be increased in some AML and chronic myeloid leukemia (CML) patients, which is associated with poorer prognosis, in addition to abnormal expression of BCL-2 and CD34 (18,21-23). Its potential role as a therapeutic target in human leukemia has also been reported by demonstrating that Axl inhibition, achieved through shRNA or small molecule inhibitors, increased apoptosis and inhibited proliferation of AML/CML cell lines and patient cells in vitro and in vivo (21,23-25). AML cells stimulate BM-derived stroma cells to upregulate GAS6, which increases the chemo-resistance of AML cells (21,23). Thus, targeting the GAS6/Axl activity is consequently a rational new treatment strategy in AML. Several Axl and/or MER inhibitors for treating solid tumors and AML/CML are in various stages of development (19). However, many are multi-kinase inhibitors; off-target effects and/or toxicity on healthy hematopoietic cells remain challenging, and most studies were performed with cell lines and unpurified or CD34+ bulk AML cells (19,21,26,27). Little is known about whether the GAS6/Axl pathway is specifically activated in subgroups of AML patients with specific chromosomal abnormalities or mutations, or in certain subpopulation(s) that might express the highest levels of Axl and other family members and hence, would be most sensitive to Axl inhibition. It is also not known if Axl inhibitors can sensitize AML stem and progenitor cells to chemotherapy or targeted therapeutics, since these cells are highly resistant to current anti-cancer therapies (12-14,17).

The BCL-2 family of proteins is known as an important gatekeeper to the apoptotic response. This group of structurally related proteins comprises pro-apoptotic and anti-apoptotic members that interact with one another. Short sequences of amino acids common to BCL-2 and other members of this protein family are known as BCL-2 homology (BH) motifs. At least one BH motif is contained in each of the BCL-2 family members. These motifs, in part, contribute to the function of each member. The BCL-2 family members can be classified into 3 functional groups: anti-apoptotic proteins such as BCL-2, pro-apoptotic effectors, and pro-apoptotic activators. Preclinical data suggest that activators, which contain only a single BH3 motif, are important mediators in the cellular response to stresses such as DNA damage. Effectors are those BCL-2 proteins closely associated with the mitochondrial membrane, and when stimulated by BH3-only activators, promote the formation of pores in the mitochondrial membrane, initiating the apoptotic program. Tumor cells may become dependent on BCL-2 for survival. Similar to oncogene addiction, in which tumor cells rely on a single dominant gene for survival, tumor cells may also become dependent on BCL-2 in order to survive. In response to stress signals, malignant cells may express pro-apoptotic activators. Some cancer cells overexpress BCL-2, which can dampen this pro-apoptotic response. The result is in many cases an abundance of pro-apoptotic activators bound and sequestered by BCL-2. In this scenario, cancer cells are thought to be primed for apoptosis, in that they may contain sufficient amounts of the pro-apoptotic activators, if displaced from BCL-2, to induce programmed cell death. Cancers that depend on BCL-2 for survival in this way are likely to be sensitive to BCL-2 modulation.

The present disclosure describes the synergistic effect of concurrently targeting Axl and BCL-2 for treating blood cancer, in particular, AML. By concurrently administering an Axl inhibitor and a BCL-2 inhibitor to a patient in need, the combination therapy provides superior therapeutic outcomes to those of monotherapies or other current combination therapies utilizing Axl inhibitors.

In particular, it is demonstrated herein synergistic effect against models of acute myeloid leukemia. As set forth the Examples, the synergistic effect was observed in multiple models of acute myeloid leukemia, including both in vitro and in vivo biological assays, and across multiple AML cell lines.

More specifically, drug combinations of an Axl inhibitor, Compound A with a BCL-2 inhibitor (ABT-199 or ABT-263) were tested, in vitro, using Molm-13 and MV4-11 AML cell lines. The BCL-2 sensitive cell lines demonstrated increased sensitivity to ABT-199 and ABT-263 when combined with Compound A, relative to ABT-199 or ABT-263 monotherapy. Combination Index (CI) analysis of the data provided indices that were less than 1, indicating that both combinations of Axl inhibitor Compound A with BCL-2 inhibitor ABT-199 or ABT-263, respectively, produced synergistic effects on both of the AML cell lines. See e.g., Example 1.

Additionally, the drug combination of the Axl inhibitor (Compound A) with the BCL-2 inhibitor (ABT-199) was demonstrated in an in vivo assay to be more effective in targeting primitive leukemic cells and/or to prevent leukemia development than Compound A alone. Briefly, a patient-derived xenograft model assay was developed in mice using purified CD34+ stem and progenitor cells from AML patients that were transduced with a GFP/Luciferase lentivirus reporter to allow non-invasive in vivo imaging (IVIS) of the mice to track leukemia development. Surprisingly, the Compound A/ABT-199 combination was highly effective at delaying and eliminating leukemia development at early time points, whereas single agent monotherapy displayed leukemia progression.

Euthanized mice were further checked for splenomegaly (enlarged spleen) and for the presence of leukemic cells in peripheral blood (PB) and bone marrow (BM) via fluorescence-activated cell sorting (FACS) analysis. Spleen size and weight for the combination therapy group was consistent with that from non-leukemic mice. In contrast, the single agent monotherapy groups demonstrated increased size and weight in the spleens. Likewise, the combination therapy group demonstrated reduced presence of leukemic cells in PB and BM relative to subjects receiving monotherapy. Additionally, survival curves for control and treatment groups demonstrated significant differences (P<0.05) between the combination and monotherapy treatment groups. In conclusion, the combined treatment with Compound A and ABT-199 decreases leukemia burden and enhances survival of leukemic mice significantly in a patient-derived xenograft (PDX) model with primary AML patient cells. See e.g., Example 3.

Moreover, efficacy and safety of the drug combination of the Axl inhibitor (Compound A) with the BCL-2 inhibitor (ABT-199) were demonstrated in animal models. In particular, the combination was shown to be effective in eliminating human leukemic cells in vivo when compared to monotherapies with Compound A alne or ABT-199 alone. Briefly, a cell-line based xenograft mouse study was performed using MV4-11 cells transduced with a GFP/Luciferase lentivirus vector to allow both sorting/analyzing of human leukemic cells in mice and the non-invasive in vivo imaging (IVIS) of the mice to track leukemia development and leukemia forming sites. Notably, the Compound A/ABT-199 combination therapy was highly effective at eliminating leukemia development as the bioluminescent signal observed after treatment was below the detection threshold. Conversely, while single agent monotherapy with Compound A also lowered bioluminescent signals but to a lesser extent, vehicle and ABT-199 monotherapy all displayed aggressive leukemia progression. Euthanized mice were further checked for spleen (splenomegaly) and liver leukemic cell infiltration and for the presence of leukemic cells in peripheral blood (PB), bone marrow (BM), spleen and liver via fluorescence-activated cell sorting (FACS) analysis. Spleen size and weight for the combination therapy group, as well as Compound A monotherapy, was consistent with that from non-leukemic mice. Conversely, the ABT-199 monotherapy and vehicle (control) groups demonstrated increased size and weight in the spleens. Similarly, FACS analysis showed the combination therapy group demonstrated dramatically reduced presence of GFP transduced leukemic cells in BM, PB, spleen and liver relative to subjects receiving monotherapy. Additionally, survival curves for control and treatment groups demonstrated significant differences (P<0.05) between the combination and monotherapy treatment groups. In summary, Compound A treatment alone can reduce leukemia propagating activity in vivo in this MV4-11 animal model and this inhibitory effect has been dramatically enhanced after combination treatment with ABT-199.

Combination Therapy

Described herein in more detail are therefore methods for treating blood cancer in a patient in need thereof, the method comprising concomitantly administering one or more Axl inhibitors with one or more BCL-2 family protein inhibitors ("BCL-2 inhibitors"). The resulting therapeutic effects are surprisingly greater than the mere additive effects of monotherapies using each type of inhibitors alone. Such a synergistic combination is further accompanied by low toxicity.

1. Axl Inhibitors

The Axl inhibitors suitable for the combination therapy disclosed are aminopyridine derivatives, known for being TAM family kinase inhibitors. See e.g., WO2015/081257. In particular, the Axl inhibitor is a compound having the structure of Formula (I):

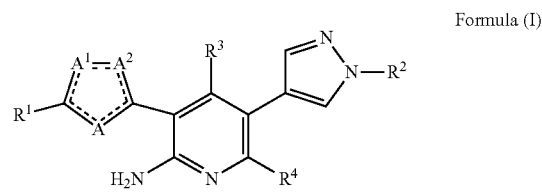

Formula (I)

wherein

A, $A^1$ and $A^2$ are the same or different and independently —N═, —$CR^5$═, or —O—;

$R^1$ is alkyl, cycloalkyl, cycloalkylalkyl, haloalkyl, aryl, aralkyl, heterocyclyl, heterocyclylalkyl, heteroaryl, or heteroarylalkyl;

$R^2$ is hydrogen, heterocyclyl, heterocyclylalkyl, cycloalkyl, alkyl, aralkyl, cycloalkylalkyl, heteroaryl, heteroarylalkyl, or aryl;

each $R^3$ and $R^4$ is the same or different and independently selected from hydrogen, alkyl, aralkyl, alkenyl, aralkenyl, alkynyl, aralkynyl, cycloalkyl, cycloalkylalkyl, halo, or haloalkyl;

$R^5$ is, at each occurrence, hydrogen, alkyl, aralkyl, cycloalkyl, cycloalkylalkyl, halo, or haloalkyl; or a stereoisomer, enantiomer or tautomer thereof, a pharmaceutically acceptable salt thereof, or a pharmaceutical composition thereof.

Of the compounds of Formula (I), another embodiment provides compounds of Formula (Ia):

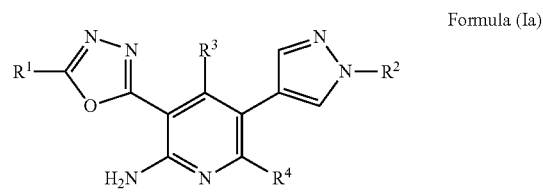

Formula (Ia)

wherein, $R^1$, $R^2$, $R^3$, and $R^4$ are as defined above.

Of the compounds of Formula (I), another embodiment provides compounds of Formula (Ib):

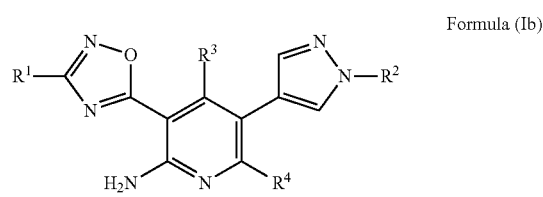

Formula (Ib)

wherein, $R^1$, $R^2$, $R^3$, and $R^4$ are as defined above.

Of the compounds of Formula (I), another embodiment provides compounds of Formula (Ic):

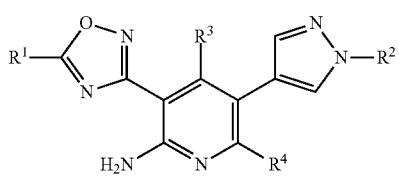

Formula (Ic)

wherein, $R^1$, $R^2$, $R^3$, and $R^4$ are as defined above.

Of the compounds of Formula (I), an embodiment provides compounds of Formula (Id):

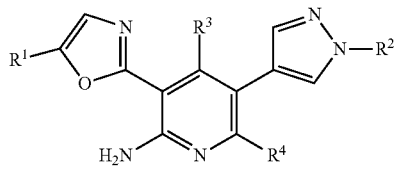

Formula (Id)

wherein:
$R^1$, $R^2$, $R^3$, and $R^4$ are as defined above.

Of the compounds of Formula (I), another embodiment provides compounds of Formula (Ie):

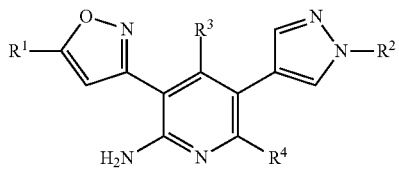

Formula (Ie)

wherein, $R^1$, $R^2$, $R^3$, and $R^4$ are as defined above.

Of the compounds of Formula (I), another embodiment provides compounds of Formula (If):

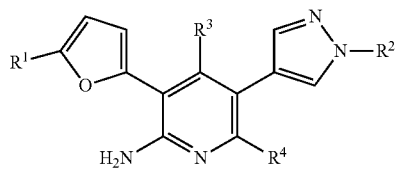

Formula (If)

wherein, $R^1$, $R^2$, $R^3$, and $R^4$ are as defined above.

In a more specific embodiment, the Axl inhibitor is a compound of formulae (I), (Ia), (Ib), (Ic), (Id), (Ie) or (If) as set forth above, wherein the compound is selected from the group consisting of:
tert-butyl-4-(4-(6-amino-5-(5-phenyloxazol-2-yl)pyridin-3-yl)-1H-pyrazol-1-yl)piperidine-1-carboxylate;
3-(5-phenyloxazol-2-yl)-5-(1-(piperidin-4-yl)-1H-pyrazol-4-yl)pyridin-2-amine;
tert-butyl 4-(4-(6-amino-5-(5-(4-chlorophenyl)oxazol-2-yl)pyridin-3-yl)-1H-pyrazol-1-yl)piperidine-1-carboxylate;
3-(5-(4-chlorophenyl)oxazol-2-yl)-5-(1-(piperidin-4-yl)-1H-pyrazol-4-yl)pyridin-2-amine;
1-(4-(4-(6-amino-5-(5-(4-chlorophenyl)oxazol-2-yl)pyridin-3-yl)-1H-pyrazol-1-yl)piperidin-1-yl)ethanone;
(4-(4-(6-amino-5-(5-(4-chlorophenyl)oxazol-2-yl)pyridin-3-yl)-1H-pyrazol-1-yl)piperidin-1-yl)(cyclopropyl)methanone;
3-(5-(3-chlorophenyl)oxazol-2-yl)-5-(1-(piperidin-4-yl)-1H-pyrazol-4-yl)pyridin-2-amine;
1-(4-(4-(6-amino-5-(5-(3-chlorophenyl)oxazol-2-yl)pyridin-3-yl)-1H-pyrazol-1-yl)piperidin-1-yl)ethanone;
3-(5-(3-chlorophenyl)oxazol-2-yl)-5-(1-(1-methylpiperidin-4-yl)-1H-pyrazol-4-yl)pyridin-2-amine;
(4-(4-(6-amino-5-(5-(3-chlorophenyl)oxazol-2-yl)pyridin-3-yl)-1H-pyrazol-1-yl)piperidin-1-yl)(cyclopropyl)methanone;
(4-(4-(6-amino-5-(5-(3-chlorophenyl)oxazol-2-yl)pyridin-3-yl)-1H-pyrazol-1-yl)piperidin-1-yl)(phenyl)methanone;
1-(4-(4-(6-amino-5-(5-(3-chlorophenyl)oxazol-2-yl)pyridin-3-yl)-1H-pyrazol-1-yl)piperidin-1-yl)-2-phenylethanone;
(4-(4-(6-amino-5-(5-(4-chlorophenyl)oxazol-2-yl)pyridin-3-yl)-1H-pyrazol-1-yl)piperidin-1-yl)(phenyl)methanone;
1-(4-(4-(6-amino-5-(5-(4-chlorophenyl)oxazol-2-yl)pyridin-3-yl)-1H-pyrazol-1-yl)piperidin-1-yl)-2-phenylethanone;
3-(5-(4-chlorophenyl)oxazol-2-yl)-5-(1-(1-methylpiperidin-4-yl)-1H-pyrazol-4-yl)pyridin-2-amine;
1-(4-(4-(6-amino-5-(5-(3-chlorophenyl)oxazol-2-yl)pyridin-3-yl)-1H-pyrazol-1-yl)piperidin-1-yl)-2,2-dimethylpropan-1-one;
(4-(4-(6-amino-5-(5-(3-chlorophenyl)oxazol-2-yl)pyridin-3-yl)-1H-pyrazol-1-yl)piperidin-1-yl)(4-fluorophenyl)methanone;
5-(1-(1-ethylpiperidin-4-yl)-1H-pyrazol-4-yl)-3-(5-phenyloxazol-2-yl)pyridin-2-amine;
3-(5-phenyloxazol-2-yl)-5-(1-(tetrahydro-2pyran-4-yl)-1H-pyrazol-4-yl)pyridin-2-amine;
3-(5-(4-chlorophenyl)oxazol-2-yl)-5-(1-(tetrahydro-2pyran-4-yl)-1H-pyrazol-4-yl)pyridin-2-amine;
3-(5-(3-chlorophenyl)oxazol-2-yl)-5-(1-cyclohexyl-1H-pyrazol-4-yl)pyridin-2-amine;
3-(5-(4-chlorophenyl)oxazol-2-yl)-5-(1-cyclohexyl-1H-pyrazol-4-yl)pyridin-2-amine;
5-(1-cyclohexyl-1H-pyrazol-4-yl)-3-(5-phenyloxazol-2-yl)pyridin-2-amine;
5-(1-(piperidin-4-yl)-1H-pyrazol-4-yl)-3-(5-(pyridin-3-yl)oxazol-2-yl)pyridin-2-amine;
5-(1-cyclohexyl-1H-pyrazol-4-yl)-3-(5-phenylisoxazol-3-yl)pyridin-2-amine;
3-(5-phenylisoxazol-3-yl)-5-(1-(tetrahydro-2H-pyran-4-yl)-1H-pyrazol-4-yl)pyridin-2-amine; 3-(5-phenylisoxazol-3-yl)-5-(1-(piperidin-4-yl)-1H-pyrazol-4-yl)pyridin-2-amine;
5-(1-(1-methylpiperidin-4-yl)-1H-pyrazol-4-yl)-3-(5-phenylisoxazol-3-yl)pyridin-2-amine;
3-(5-phenylfuran-2-yl)-5-(1-(piperidin-4-yl)-1H-pyrazol-4-yl)pyridin-2-amine;
5-(1-(1-methylpiperidin-4-yl)-1H-pyrazol-4-yl)-3-(5-phenylfuran-2-yl)pyridin-2-amine; 5-(1-cyclohexyl-1H-pyrazol-4-yl)-3-(5-phenylfuran-2-yl)pyridin-2-amine;
3-(5-phenylfuran-2-yl)-5-(1-(tetrahydro-2H-pyran-4-yl)-1H-pyrazol-4-yl)pyridin-2-amine;
tert-butyl 4-(4-(6-amino-5-(5-phenyl-1,3,4-oxadiazol-2-yl)pyridin-3-yl)-1H-pyrazol-1-yl)piperidine-1-carboxylate;
3-(5-phenyl-1,3,4-oxadiazol-2-yl)-5-(1-(piperidin-4-yl)-1H-pyrazol-4-yl)pyridin-2-amine; 3-(5-(2,6-dichloro-3-fluorophenyl)-1,3,4-oxadiazol-2-yl)-5-(1-(piperidin-4-yl)-1H-pyrazol-4-yl)pyridin-2-amine;

3-(5-(4-(tert-butyl)phenyl)-1,3,4-oxadiazol-2-yl)-5-(1-(piperidin-4-yl)-1H-pyrazol-4-yl)pyridin-2-amine;
tert-butyl 4-(4-(6-amino-5-(5-(4-(tert-butyl)phenyl)-1,3,4-oxadiazol-2-yl)pyridin-3-yl)-1H-pyrazol-1-yl)piperidine-1-carboxylate;
3-(5-(2,5-difluorophenyl)-1,3,4-oxadiazol-2-yl)-5-(1-(piperidin-4-yl)-1H-pyrazol-4-yl)pyridin-2-amine; 3-(5-(2,6-dichlorophenyl)-1,3,4-oxadiazol-2-yl)-5-(1-(piperidin-4-yl)-1H-pyrazol-4-yl)pyridin-2-amine;
tert-butyl 4-(4-(6-amino-5-(5-(2,6-dichlorophenyl)-1,3,4-oxadiazol-2-yl)pyridin-3-yl)-1H-pyrazol-1-yl)piperidine-1-carboxylate;
3-(5-(4-fluorophenyl)-1,3,4-oxadiazol-2-yl)-5-(1-(piperidin-4-yl)-1H-pyrazol-4-yl)pyridin-2-amine; tert-butyl 4-(4-(6-amino-5-(5-(4-fluorophenyl)-1,3,4-oxadiazol-2-yl)pyridin-3-yl)-1H-pyrazol-1-yl)piperidine-1-carboxylate;
1-(4-(4-(6-amino-5-(5-(2,6-dichlorophenyl)-1,3,4-oxadiazol-2-yl)pyridin-3-yl)-1H-pyrazol-1-yl)piperidin-1-yl)ethanone; 3-(5-(2,6-dichlorophenyl)-1,3,4-oxadiazol-2-yl)-5-(1-(1-methylpiperidin-4-yl)-1H-pyrazol-4-yl)pyridin-2-amine;
1-(4-(4-(6-amino-5-(5-(2,6-dichlorophenyl)-1,3,4-oxadiazol-2-yl)pyridin-3-yl)-1H-pyrazol-1-yl)piperidin-1-yl)-4-methylpentan-1-one;
(4-(4-(6-amino-5-(5-(2,6-dichlorophenyl)-1,3,4-oxadiazol-2-yl)pyridin-3-yl)-1H-pyrazol-1-yl)piperidin-1-yl)(cyclopropyl)methanone;
(4-(4-(6-amino-5-(5-(2,6-dichlorophenyl)-1,3,4-oxadiazol-2-yl)pyridin-3-yl)-1H-pyrazol-1-yl)piperidin-1-yl)(phenyl)methanone;
1-(4-(4-(6-amino-5-(5-(2,6-dichlorophenyl)-1,3,4-oxadiazol-2-yl)pyridin-3-yl)-1H-pyrazol-1-yl)piperidin-1-yl)-2-phenylethanone;
3-(5-(2,6-dichlorophenyl)-1,3,4-oxadiazol-2-yl)-5-(1-(1-ethylpiperidin-4-yl)-1H-pyrazol-4-yl)pyridin-2-amine;
3-(5-(2,6-dichlorophenyl)-1,3,4-oxadiazol-2-yl)-5-(1-(1-dodecylpiperidin-4-yl)-1H-pyrazol-4-yl)pyridin-2-amine;
tert-butyl 4-(4-(6-amino-5-(5-(pyrazin-2-yl)-1,3,4-oxadiazol-2-yl)pyridin-3-yl)-1H-pyrazol-1-yl)piperidine-1-carboxylate; tert-butyl 4-(4-(6-amino-5-(5-(pyridin-2-yl)-1,3,4-oxadiazol-2-yl)pyridin-3-yl)-1H-pyrazol-1-yl)piperidine-1-carboxylate;
5-(1-(piperidin-4-yl)-1H-pyrazol-4-yl)-3-(5-(pyrazin-2-yl)-1,3,4-oxadiazol-2-yl)pyridin-2-amine;
5-(1-(piperidin-4-yl)-1H-pyrazol-4-yl)-3-(5-(pyridin-2-yl)-1,3,4-oxadiazol-2-yl)pyridin-2-amine;
tert-butyl 4-(4-(6-amino-5-(5-(thiazol-2-yl)-1,3,4-oxadiazol-2-yl)pyridin-3-yl)-1H-pyrazol-1-yl)piperidine-1-carboxylate;
5-(1-(piperidin-4-yl)-1H-pyrazol-4-yl)-3-(5-(thiazol-2-yl)-1,3,4-oxadiazol-2-yl)pyridin-2-amine;
5-(1-(piperidin-4-yl)-1H-pyrazol-4-yl)-3-(5-(pyridin-3-yl)-1,3,4-oxadiazol-2-yl)pyridin-2-amine;
tert-butyl 4-(4-(6-amino-5-(5-(pyridin-3-yl)-1,3,4-oxadiazol-2-yl)pyridin-3-yl)-1H-pyrazol-1-yl)piperidine-1-carboxylate;
tert-butyl 4-(4-(6-amino-5-(5-(4-(trifluoromethyl)-thiazol-2-yl)-1,3,4-oxadiazol-2-yl)pyridin-3-yl)-1H-pyrazol-1-yl)piperidine-1-carboxylate;
5-(1-(piperidin-4-yl)-1H-pyrazol-4-yl)-3-(5-(4-(trifluoromethyl)thiazol-2-yl)-1,3,4-oxadiazol-2-yl)pyridin-2-amine;
tert-butyl 4-(4-(6-amino-5-(5-(cyclopropylmethyl)-1,3,4-oxadiazol-2-yl)pyridin-3-yl)-1H-pyrazol-1-yl)piperidine-1-carboxylate;
3-(5-(cyclopropylmethyl)-1,3,4-oxadiazol-2-yl)-5-(1-(piperidin-4-yl)-1H-pyrazol-4-yl)pyridin-2-amine;
tert-butyl 4-(4-(6-amino-5-(5-benzyl-1,3,4-oxadiazol-2-yl)pyridin-3-yl)-1H-pyrazol-1-yl)piperidine-1-carboxylate;
3-(5-benzyl-1,3,4-oxadiazol-2-yl)-5-(1-(piperidin-4-yl)-1H-pyrazol-4-yl)pyridin-2-amine; 3-(5-(2,6-dichlorophenyl)-1,3,4-oxadiazol-2-yl)-5-(1H-pyrazol-4-yl)pyridin-2-amine; 3-(5-phenyl-1,3,4-oxadiazol-2-yl)-5-(1H-pyrazol-4-yl)pyridin-2-amine;
3-(5-(4-(tert-butyl)phenyl)-1,3,4-oxadiazol-2-yl)-5-(1H-pyrazol-4-yl)pyridin-2-amine; 3-(5-(2,5-difluorophenyl)-1,3,4-oxadiazol-2-yl)-5-(1H-pyrazol-4-yl)pyridin-2-amine;
3-(5-(4-fluorophenyl)-1,3,4-oxadiazol-2-yl)-5-(1H-pyrazol-4-yl)pyridin-2-amine; 5-(1-cyclohexyl-1H-pyrazol-4-yl)-3-(5-(2,6-dichlorophenyl)-1,3,4-oxadiazol-2-yl)pyridin-2-amine;
5-(1-cyclohexyl-1H-pyrazol-4-yl)-3-(5-phenyl-1,3,4-oxadiazol-2-yl)pyridin-2-amine;
3-(5-(2,6-dichlorophenyl)-1,3,4-oxadiazol-2-yl)-5-(1-(tetrahydro-2H-pyran-4-yl)-1H-pyrazol-4-yl)pyridin-2-amine;
3-(5-phenyl-1,3,4-oxadiazol-2-yl)-5-(1-(tetrahydro-2H-pyran-4-yl)-1H-pyrazol-4-yl)pyridin-2-amine; 3-(3-phenyl-1,2,4-oxadiazol-5-yl)-5-(1-(piperidin-4-yl)-1H-pyrazol-4-yl)pyridin-2-amine;
1-(4-(4-(6-amino-5-(3-phenyl-1,2,4-oxadiazol-5-yl)pyridin-3-yl)-1H-pyrazol-1-yl)piperidin-1-yl)ethanone;
(4-(4-(6-amino-5-(3-phenyl-1,2,4-oxadiazol-5-yl)pyridin-3-yl)-1H-pyrazol-1-yl)piperidin-1-yl)(cyclopropyl)methanone;
5-(1-(1-methylpiperidin-4-yl)-1H-pyrazol-4-yl)-3-(3-phenyl-1,2,4-oxadiazol-5-yl)pyridin-2-amine;
(4-(4-(6-amino-5-(3-phenyl-1,2,4-oxadiazol-5-yl)pyridin-3-yl)-1H-pyrazol-1-yl)piperidin-1-yl)(phenyl)methanone;
1-(4-(4-(6-amino-5-(3-phenyl-1,2,4-oxadiazol-5-yl)pyridin-3-yl)-1H-pyrazol-1-yl)piperidin-1-yl)-2-phenylethanone;
3-(3-(2,6-dichlorophenyl)-1,2,4-oxadiazol-5-yl)-5-(1-(piperidin-4-yl)-1H-pyrazol-4-yl)pyridin-2-amine;
3-(3-(2,6-dichlorophenyl)-1,2,4-oxadiazol-5-yl)-5-(1-(1-methylpiperidin-4-yl)-1H-pyrazol-4-yl)pyridin-2-amine;
3-(3-(2,6-dichlorophenyl)-1,2,4-oxadiazol-5-yl)-5-(1-(1-ethylpiperidin-4-yl)-1H-pyrazol-4-yl)pyridin-2-amine;
5-(1-(1-ethylpiperidin-4-yl)-1H-pyrazol-4-yl)-3-(3-phenyl-1,2,4-oxadiazol-5-yl)pyridin-2-amine;
3-(3-(2,6-dichlorophenyl)-1,2,4-oxadiazol-5-yl)-5-(1-(1-dodecylpiperidin-4-yl)-1H-pyrazol-4-yl)pyridin-2-amine;
5-(1-cyclohexyl-1H-pyrazol-4-yl)-3-(3-phenyl-1,2,4-oxadiazol-5-yl)pyridin-2-amine; 5-(1-cyclohexyl-1H-pyrazol-4-yl)-3-(3-(2,6-dichlorophenyl)-1,2,4-oxadiazol-5-yl)pyridin-2-amine;
3-(3-phenyl-1,2,4-oxadiazol-5-yl)-5-(1-(tetrahydro-2H-pyran-4-yl)-1H-pyrazol-4-yl)pyridin-2-amine
3-(3-(2,6-dichlorophenyl)-1,2,4-oxadiazol-5-yl)-5-(1-(tetrahydro-2H-pyran-4-yl)-1H-pyrazol-4-yl)pyridin-2-amine;
3-(3-phenyl-1,2,4-oxadiazol-5-yl)-5-(1H-pyrazol-4-yl)pyridin-2-amine;
5-(1-cyclohexyl-1H-pyrazol-4-yl)-3-(5-phenyl-1,2,4-oxadiazol-3-yl)pyridin-2-amine;
3-(5-phenyl-1,2,4-oxadiazol-3-yl)-5-(1-(tetrahydro-2H-pyran-4-yl)-1H-pyrazol-4-yl)pyridin-2-amine;
3-(5-phenyl-1,2,4-oxadiazol-3-yl)-5-(1-(piperidin-4-yl)-1H-pyrazol-4-yl)pyridin-2-amine;
5-(1-(1-methylpiperidin-4-yl)-1H-pyrazol-4-yl)-3-(5-phenyl-1,2,4-oxadiazol-3-yl)pyridin-2-amine;
3-(5-(2,5-dichlorophenyl)-1,2,4-oxadiazol-3-yl)-5-(1-(piperidin-4-yl)-1H-pyrazol-4-yl)pyridin-2-amine; or
3-(5-phenyl-1,2,4-oxadiazol-3-yl)-5-(1H-pyrazol-4-yl)pyridin-2-amine.

In preferred embodiments, the combination therapy utilizes an Axl inhibitor having the structure represented by Formula (Ia).

In more preferred embodiment, the Axl inhibitor is 3-(5-(cyclopropylmethyl)-1,3,4-oxadiazol-2-yl)-5-(1-(piperidin-4-yl)-1H-pyrazol-4-yl)pyridin-2-amine.

The Axl inhibitors described herein may be prepared according to the methods disclosed in WO2015/081257, which is incorporated herein by reference in its entirety.

2. BCL-2 Family Protein Inhibitors

According to various embodiments, the BCL-2 inhibitor suitable for the combination therapy is a compound of Formula (II):

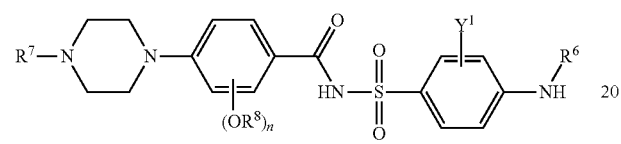

Formula (II)

wherein n is 0 or 1;

$R^6$ is optionally substituted heterocyclylalkyl, optionally substituted cycloalkylalkyl or optionally substituted heteroalkyl;

$R^7$ is optionally substituted heterocyclylalkyl;

$R^8$ is optionally substituted heteroaryl or optionally substituted aryl;

$Y^1$ is an electron-withdrawing group, a stereoisomer, enantiomer or tautomer thereof, a pharmaceutically acceptable salt thereof, or a pharmaceutical composition thereof.

In more specific embodiments, the BCL-2 inhibitor is a compound of Formula (II), wherein $R^6$ is heteroalkyl or heterocyclylalkyl.

In more specific embodiments, $R^6$ is heteroalkyl having the following structure:

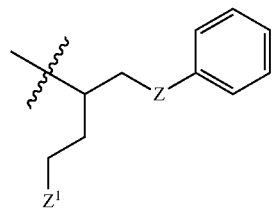

wherein

Z is —O—, —S— or —NH;

$Z^1$ is heterocyclyl. In more specific embodiments, $Z^1$ is azepan-1-yl, morpholin-1-yl, 1,4-oxazepan-4-yl, pyrrolidin-1-yl, —N(CH$_3$)$_2$, —N(CH$_3$)(CH(CH$_3$)$_2$), 7-azabicyclo[2.2.1]heptan-1-yl or 2-oxa-5-azabicyclo[2.2.1]hept-5-yl.

In specific embodiments, $R^7$ is

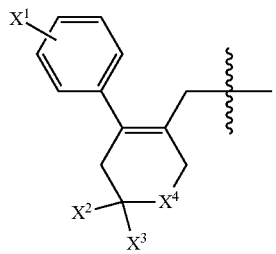

wherein $X^1$ is H, F, Cl, Br, or I;

$X^2$ and $X^3$ are independently hydrogen or alkyl; and $X^4$ is —O—, —C(R$^9$)$_2$—, or —CH$_2$CH$_2$—; and $R^9$ is hydrogen or alkyl.

In a more specific embodiment, the BCL-2 inhibitor has a structure of Formula (IIa) or Formula (IIb):

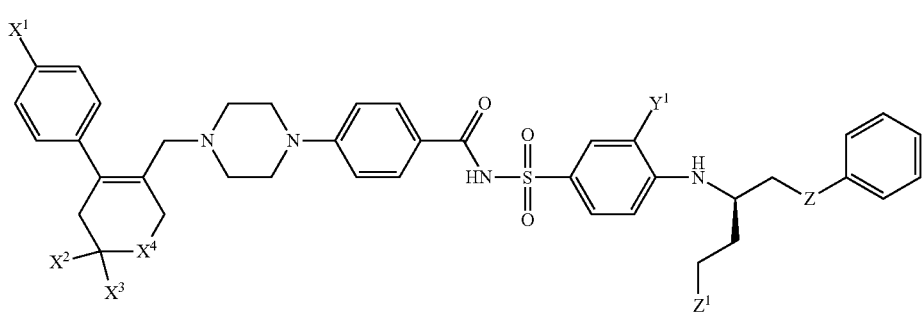

Formula (IIa)

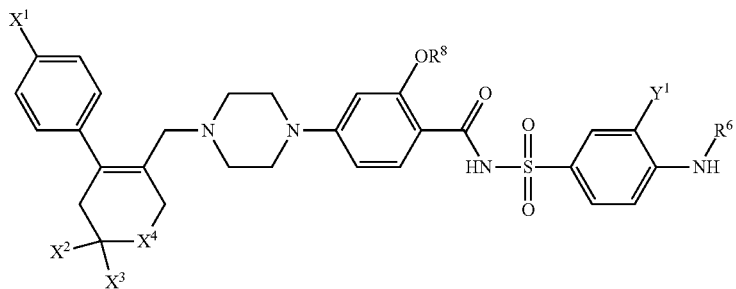

Formula (IIb)

wherein, $R^6$, $R^8$, $X^1$, $X^2$, $X^3$, $X^4$, $Y^1$, Z and $Z^1$ are as defined above.

In various embodiments, $R^8$ is heteroaryl optionally substituted with one or more substituents selected from the group consisting of alkyl, $NH_2$, and halo.

In more specific embodiments, $R^8$ is 1H-Pyrrolo[2,3-b]pyridin-5-yl.

In various embodiments, $Y^1$ is —CN, —$NO_2$, —$SO_2C(X^5)_3$, —$CF_3$, F, Cl, or Br; wherein each $X^5$ is, at each occurrence, independently, H, F or Cl.

In more specific embodiments, $Y^1$ is —$NO_2$, or —$SO_2CF_3$.

The BCL-2 inhibitors of Formula (II), (IIa) and (IIb), as set forth above, may be prepared according to the processes disclosed in U.S. Pat. No. 7,390,799 and Published U.S. Pat. No. 9,345,702, which are incorporated by reference in their entireties.

In a preferred embodiment the one or more BCL-2 inhibitors is Venetoclax (VENCLEXTA®/ABT-199), or Navitoclax (ABT-263):

(ABT-199)

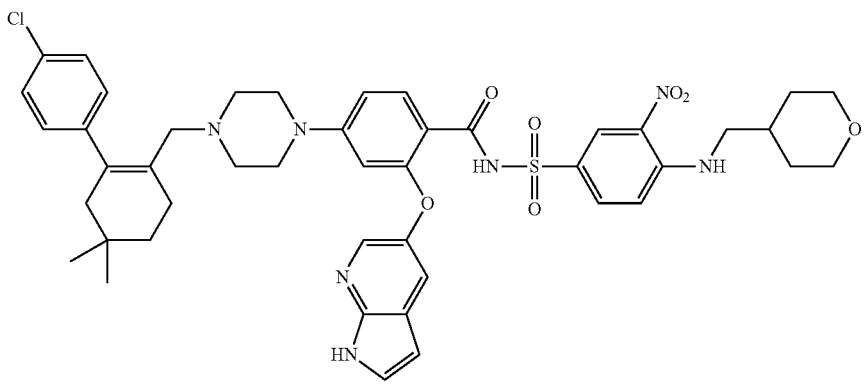

Venetoclax (ABT-263)

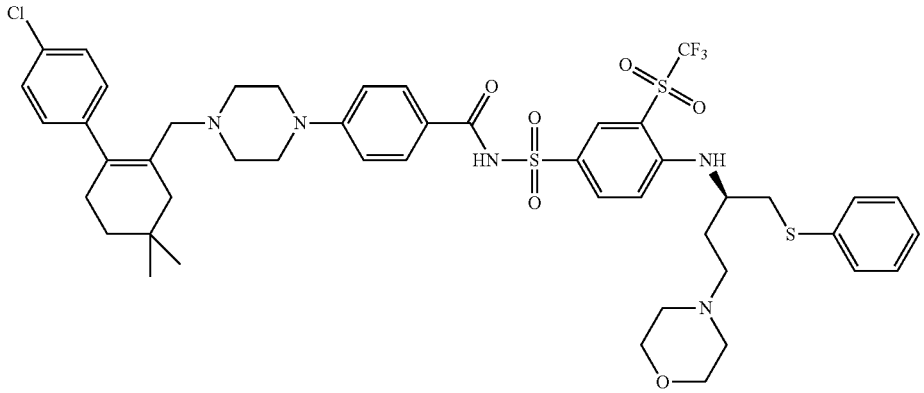

Navitoclax

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Amino" refers to the —$NH_2$ radical.

"Methoxy" refers to the —$OCH_3$ radical.

"Cyano" refers to the —CN radical.

"Nitro" refers to the —$NO_2$ radical.

"Trifluoromethyl" refers to the —$CF_3$ radical.

"Oxo" refers to the =O.

"Thioxo" refers to the =S.

"Acyl" refers to —C(O)$R^{14}$ radical, wherein $R^{14}$ is hydrogen, alkyl, haloalkyl, cycloalkyl, cycloalkylalkyl, aryl, aralkyl, heterocyclyl, heterocyclylalkyl, heteroaryl or heteroarylalkyl.

"Alkyl" refers to a straight or branched hydrocarbon chain radical, when unsubstituted, consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one or more substituents, as defined herein. "Alkenyl" refers to a straight or branched hydrocarbon chain radical group, when unsubstituted, consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of or more substituents, as defined herein.

"Alkynyl" refers to a straight or branched hydrocarbon chain radical group, when unsubstituted, consisting solely of carbon and hydrogen atoms, containing at least one triple bond, optionally containing at least one double bond, having from two to twelve carbon atoms, preferably one to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted by one or more substituents, as defined herein. "Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkoxy" refers to a radical of the formula —O$R_a$ where $R_a$ is an alkyl radical as defined above. The alkyl part of the alkoxy radical may be optionally substituted as defined above for an alkyl radical.

"Aryl" refers to aromatic monocyclic or multi-cyclic hydrocarbon ring system, when unsubstituted, consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents, as defined herein. "Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Aralkenyl" refers to a radical of the formula —$R_cR_b$ where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aralkynyl" refers to a radical of the formula —$R_dR_b$ where $R_d$ is an alkynyl radical as defined above and $R_b$ is one or more aryl radicals as defined above. The aryl part of the aralkynyl radical may be optionally substituted as described above for an aryl group. The alkynyl part of the aralkynyl radical may be optionally substituted as defined above for an alkynyl group.

"Cycloalkyl" refers to a stable non-aromatic monocyclic or bicyclic hydrocarbon radical, when unsubstituted, consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents, as defined herein. "Cycloalkylalkyl" refers to a radical of the formula —$R_an_d$ where $R_a$ is an alkyl radical as defined above and $R_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"Electron withdrawing group" refers to groups that reduce electron density of the moiety to which they are attached (relative to the density of the moiety without the substituent). Such groups include, for example, —F, —Cl, —Br, —I, —CN, —$CF_3$, —$NO_2$, —C(O)H, —C(O)alkyl, —C(O)

Oalkyl, —C(O)OH, —C(O)Cl, and —S(O)$_2$R (wherein R is alkyl, haloalkyl, OH, NH$_2$, and the like).

"Halo" refers to bromo, chloro, fluoro or iodo.

"Haloalkyl" refers to an alkyl radical, as defined above, that is substituted by one or more halo radicals, as defined above. One or more carbons of the alkyl radical may be substituted by the one or more halo radicals. Examples of haloalkyl include, trifluoromethyl, difluoromethyl, trichloromethyl, 2,2,2-trifluoroethyl, 1-fluoromethyl-2-fluoroethyl, 3-bromo-2-fluoro-propyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3-bromoprop-1-enyl, and the like. The alkenyl part of the haloalkenyl radical may be optionally substituted as defined above for an alkyl group.

"Heteroalkyl" refers to a stable straight or branched chain, or combinations thereof, including at least one carbon atom and at least one heteroatom (e.g., selected from the group consisting of O, N, P, Si, and S), and wherein the nitrogen and sulfur atoms may optionally be oxidized, and the nitrogen heteroatom may optionally be quaternized. The heteroatom(s) (e.g., O, N, P, S, B, As, and Si) may be placed at any interior position of the heteroalkyl group or at the position at which the alkyl group is attached to the remainder of the molecule. Examples include, but are not limited to: —CH$_2$—CH$_2$—O—CH$_3$—, —CH$_2$—CH$_2$—N—CH$_3$, —CH$_2$—CH$_2$—S—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, and —CN. Up to two or three heteroatoms may be consecutive, such as, for example, —CH$_2$—O—Si(CH$_3$)$_3$. Although heteroalkyl chain is non-cyclic, it may be further substituted by a cyclic moiety, including for example, aryl (e.g., phenyl), heterocyclyl (e.g., morpholin-1-yl), heteroaryl, cycloalkyl, and the like.

"Heterocyclyl" refers to a stable 3- to 18-membered non-aromatic ring radical including, as ring atoms, at least one carbon atom and from one to five heteroatoms selected from the group consisting of nitrogen, oxygen and sulfur. For purposes of this disclosure, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; and the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above which are optionally substituted by one or more substituents, as defined herein.

"Heterocyclylalkyl" refers to a radical of the formula —R$_a$R$_e$ where R$_a$ is an alkyl radical as defined above and R$_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical including, as ring atoms, at least one carbon atom and from one to five heteroatoms selected from the group consisting of nitrogen, oxygen and sulfur. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; and the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrrolo[2,3-b]pyridinyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents, as defined herein. Heteroaryl, as defined herein, may be monovalent or divalent. When heteroaryl is a substituent of another moiety, the heteroaryl is monovalent, which means that the heteroaryl is connected to the other moiety by a single ring atom. An example of a monovalent heteroaryl can be found in the radical of heteroarylalkyl, in which an alkyl group is substituted with a heteroaryl group.

"Heteroarylalkyl" refers to a radical of the formula —R$_a$R$_f$ where R$_a$ is an alkyl radical as defined above and R$_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkenyl" refers to a radical of the formula —R$_c$R$_g$ where R, is an alkenyl radical as defined above and R$_g$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"N-heteroaryl" is a subset of heteroaryl, and refers to a heteroaryl having at least one nitrogen ring atom. Heteroaryl is otherwise as defined as herein. Examples of N-heteroaryls include, without limitation, benzimidazolyl, benzindolyl, benzotriazolyl, benzo[4,6]imidazo[1,2-a]pyridinyl, carbazolyl, cinnolinyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl.

"Substituent" refers to a radical (a single non-hydrogen atom or a functional group) that is or can be bonded to another molecule. An substituent is therefore any one of the following radicals: alkyl, alkenyl, amino, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —OR$^{14}$, —OC(O)R$^{14}$, —N(R$^{14}$)$_2$, —C(O)R$^{14}$, —C(O)OR$^{14}$, —C(O)N(R$^{14}$)$_2$, —N(R$^{14}$)C(O) OR$^{16}$, —N(R$^{14}$)C(O)R$^{16}$, —N(R$^{14}$)(S(O)$_t$R$^{16}$) (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Prodrugs" refers to a compound that may be converted under physiological conditions or by solvolysis to a biologically active compound of Formulae (I) or (II) or any one of the respective substructures. Thus, the term "prodrug" refers to a metabolic precursor of a compound Formulae (I) or (II) or any one of the respective substructures that is pharmaceutically acceptable; the latter is also referred to as a "parent compound." A prodrug may be inactive when administered to a subject in need thereof, but is converted in vivo to an active compound, i.e., the parent compound. Prodrugs are typically rapidly transformed in vivo to yield the parent compound, for example, by hydrolysis in blood.

The term "prodrug" is also meant to include any covalently bonded carriers which release the active compound of the disclosure in vivo when such prodrug is administered to a mammalian subject. Prodrugs of a compound of the disclosure may be prepared by modifying functional groups present in the compound of Formula (I) or any one of the substructures in such a way that the modifications are cleaved, either in routine manipulation or in vivo, to the parent compound. Prodrugs include compounds of the disclosure wherein a hydroxy, amino or mercapto group is bonded to any group that, when the prodrug disclosure is administered to a mammalian subject, cleaves to restore the free hydroxy, free amino or free mercapto group, respectively. Examples of prodrugs include, but are not limited to, acetate, formate and benzoate, and phosphate derivatives of alcohol or amine functional groups in the compounds of Formula (I), (II) or any one of the sub structures.

"Mammal" or "mammalian subject" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the disclosure which, when administered to a mammal, preferably a human, is sufficient to effect treatment, as defined below, of a disease or condition in the mammal, preferably a human. The amount of a compound of the disclosure which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development or reversing its progression; or (iii) relieving the disease or condition, i.e., causing regression of the disease or condition.

The compounds of the disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, such as HPLC using a chiral column.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposeable mirror images of one another.

A "tautomer" refers to a proton shift from one atom of a molecule to another atom of the same molecule. The present disclosure includes tautomers of any said compounds.

Where a bond is shown as a dashed line (---), it is understood that the location allows for the possibility of a double bond. For example, the structure of the linker "A"-ring moiety is shown as:

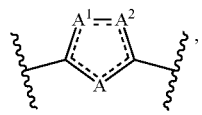

in which each dash bond may, but not necessarily, indicate the presence of a double bond. For instance, when A is —NH═, A is connected to the two adjacent carbon atoms by a single bond and a double bond, respectively. On the other hand, if A is defined as —O—, A is connected to the two adjacent carbon atoms by single bonds, respectively. The location and number of the double bonds in a given "A"-ring structure should satisfy the valence requirement, as would be recognized by a skilled person in the art.

Administration of the Combination Therapy

According to various embodiments, one or more Axl inhibitors, preferably a compound of Formula (I) or any one of the substructures represented by Formulae (Ia)-(If), is used as an active ingredient in combination with one or more BCL-2 inhibitors, preferably a compound of Formula (II), or any one of the substructures represented by Formulae (IIa)-(IIb). The combined therapy is efficacious in preventing, treating or managing one or more blood cancers.

As used herein, blood cancer refers to any one of the three main types of hematological cancers, namely, leukemia, lymphoma and myeloma. The combination therapy is particularly efficacious against AML.

Advantageously, such combination therapies exert greater than additive effects, i.e., synergistic effects, when compared to each therapy administered individually. Accordingly, as used herein "combination therapy" refers to the administration of one or more Axl inhibitor, (e.g., a compound of Formula (I)), in combination with the administration of one or more BCL-2 inhibitors. Unless stated otherwise, "combination therapy" may include simultaneous or sequential administration of the Axl inhibitor and the BCL-2 inhibitor, in any order, in any dosage forms.

The combination therapies of the invention are useful in preventing, treating or managing one or more blood cancers, in particular, leukemia. Examples of leukemia include acute leukemia, acute lymphocytic leukemia, acute myelocytic leukemia such as myeloblastic, promyelocytic, myelomonocytic, monocytic, erythroleukemia leukemia and myelodysplastic syndrome, chronic leukemia such as but not limited to, chronic myelocytic (granulocytic) leukemia, chronic lymphocytic leukemia, hairy cell leukemia.

The antiproliferative effect of a combination therapy of the invention may be assessed by administering the active ingredients of the combination therapy to a cultured tumor cell line. In the context of an in vitro assay, administration of an active ingredient may be simply achieved by contacting the cells in culture with the active ingredient in amounts effective to inhibit cell proliferation. Alternatively, the antiproliferative effect of a combination therapy of the invention may be assessed by administering the active ingredients of the combination therapy to an animal in an approved in vivo model for cell proliferation.

The combination therapies of the invention can be tested for the treatment of leukemia and lymphoma by testing the combination therapy in the xenograft in SCID mouse model using human Axl-expressing cancer cell lines including, but not limited to, Molm-13, MV4-11, HeLa, MDA-MB-231, SK-OV-3, OVCAR-8, DU145, H1299, ACHN, A498 and Caki-1. In addition, the combination therapy may be tested for its use in treating leukemia in the xenograft in SCID or nu/nu mouse model using human Axl-expressing AML and CML leukemia cell lines.

Selection of the preferred prophylactically or therapeutically effective dose of an active ingredient used in the combination therapies of the invention can be determined (e.g., by clinical trials) by a skilled artisan based upon the consideration of several factors, including the activity of the specific compound employed; the metabolic stability and length of action of the compound; the age, body weight, general health, sex, and diet of the patient; the mode and time of administration; the rate of excretion; the drug combination; and the severity of the metastatic cancer.

The precise dose of either the Axl inhibitor or the one or more BCL-2 inhibitors used in the combination therapies of the invention will also depend on the route of administration and the seriousness of the leukemia and should be decided according to the judgment of the medical practitioner and each patient's circumstances. Effective doses may be extrapolated from dose-response curves derived from in vitro or animal model test systems.

For example, a therapeutically effective daily dose for a Axl inhibitor or a BCL-2 inhibitor may be, for a 70 kg mammal, from about 0.001 mg/kg (i.e., 0.07 mg) to about 300 mg/kg (i.e., 21.0 gm); preferably a therapeutically effective dose is from about 0.01 mg/kg (i.e., 0.7 mg) to about 100 mg/kg (i.e., 7.0 gm); more preferably a therapeutically effective dose is from about 0.1 mg/kg (i.e., 7 mg) to about 50 mg/kg (i.e., 3.5 gm); and more preferably a therapeutically effective dose is from about 0.5 mg/kg (i.e., 35 mg) to about 25 mg/kg (i.e., 1.75 gm).

Preferably, the invention provides for any method of administering lower doses of the one or more BCL-2 inhibitors used in the combination therapies of the invention than previously known to be effective for the prevention, treatment and management of blood cancers. Even more preferably, lower doses of the one or more BCL-2 inhibitors are administered in the combination therapies of the invention with lower doses of the Axl inhibitor.

In the combination therapies of the invention, an Axl inhibitor is administered simultaneously with, prior to, or after administration of one or more BCL-2 inhibitors, as described herein, by the same route of administration or by different routes. Such combination therapy includes administration of a single pharmaceutical dosage formulation which contains an Axl inhibitor and one or more additional chemotherapeutic agents, as well as administration of the Axl inhibitor and each BCL-2 inhibitor in its own separate pharmaceutical dosage formulation. For example, the Axl inhibitor and the other one or more BCL-2 inhibitors can be administered to the patient together in a single oral dosage composition such as a tablet or capsule, or each agent can be administered in separate oral dosage formulations. Where separate dosage formulations are used, the Axl inhibitor and the one or more BCL-2 inhibitors can be administered to the patient at essentially the same time, i.e., concurrently, or at separately staggered times, i.e., sequentially. All such combinations of administration are encompassed by the combination therapies of the invention.

In certain embodiments of the combination therapies of the invention, the Axl inhibitor is administered to a patient concomitantly with one or more BCL-2 inhibitors useful for the treatment of cancer. The term "concomitantly" or "concurrently," is not limited to the administration of the active ingredients (i.e., the Axl inhibitor and the one or more BCL-2 inhibitors) at exactly the same time, but rather it is meant that the Axl inhibitor and the BCL-2 inhibitor(s) are administered to a patient in a sequence and within a time interval such that the TAM inhibitor can act together with the BCL-2 inhibitor(s) to provide an synergistic benefit than if they were administered otherwise. For example, each active ingredient of the combination therapies of the invention may be administered at the same time or sequentially in any order at different points in time; however, if not administered at the same time, they should be administered sufficiently close in time so as to provide the desired therapeutic or prophylactic effect. For example, the chemotherapeutic agent may be administered one time per week and the Axl inhibitor may be administered every day. In other words, the dosing regimens for the active ingredients are carried out concurrently even if the active ingredients are not administered simultaneously or within the same patient visit.

In certain embodiments, the active ingredients of the invention are cyclically administered to a patient. Cycling therapy involves the administration of a first active ingredient, such as the Axl inhibitor, for a period of time, followed by the administration of the second and/or third active ingredient for a period of time and repeating this sequential administration. Cycling therapy can reduce the development of resistance to one or more of the therapies, avoid or reduce the side effects of one of the therapies, and/or improves the efficacy of the treatment.

In yet other embodiments, the active ingredients of the combination therapies of the invention are administered in metronomic dosing regimens, either by continuous infusion or frequent administration without extended rest periods. Such metronomic administration can involve dosing at constant intervals without rest periods. Typically the chemotherapeutic agents, in particular cytotoxic agents, are used at lower doses. Such dosing regimens encompass the chronic daily administration of relatively low doses for extended periods of time. In one embodiment, the use of lower doses of the chemotherapeutic agent can minimize toxic side effects and eliminate rest periods. In certain embodiments, the active ingredients are administered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled oncologist.

In a preferred embodiment, the Axl inhibitor is administered every 24 hours to the patient and the one or more BCL-2 inhibitors is administered 24 hours.

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

Administration of the compounds of the disclosure, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the disclosure in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the disclosure, or a pharmaceutically acceptable salt thereof, for treatment of a disease or condition of interest in accordance with the teachings of this disclosure.

A pharmaceutical composition of the disclosure may be in the form of a solid or liquid. In one aspect, the carrier(s) are particulate, so that the compositions are, for example, in tablet, capsule, or powder form. The carrier(s) may be liquid, with the compositions being, for example, an oral oil, injectable liquid or an aerosol, which is useful in, for example, inhalatory administration.

REFERENCES (1) Dohner H, Estey E H, Amadori S et al. Diagnosis and management of acute myeloid leukemia in adults: recommendations from an international expert panel, on behalf of the European Leukemia Net. Blood. 2010; 115:453-474.
(2) Khwaja A, Bjorkholm M, Gale R E et al. Acute myeloid leukaemia. Nat Rev Dis Primers. 2016; 2:16010.
(3) Dohner H, Weisdorf D J, Bloomfield C D. Acute Myeloid Leukemia. N Engl J Med. 2015; 373:1136-1152.
(4) Ley T J, Miller C, Ding L et al. Genomic and epigenomic landscapes of adult de novo acute myeloid leukemia. N Engl J Med. 2013; 368:2059-2074.
(5) Altieri D C. AML therapy: wake up the guardian and cut loose the executioners. Cancer Cell. 2017; 32:719-720.
(6) Papaemmanuil E, Gerstung M, Bullinger L et al. Genomic Classification and Prognosis in Acute Myeloid Leukemia. N Engl J Med. 2016; 374:2209-2221.
(7) Burnett A, Wetzler M, Lowenberg B. Therapeutic advances in acute myeloid leukemia. J Clin Oncol. 2011; 29:487-494.
(8) Kantarjian H. Acute myeloid leukemia—major progress over four decades and glimpses into the future. Am J Hematol. 2016; 91:131-145.
(9) Tamamyan G, Kadia T, Ravandi F et al. Frontline treatment of acute myeloid leukemia in adults. Crit Rev Oncol Hematol. 2017; 110:20-34.
(10) Dombret H, Gardin C. An update of current treatments for adult acute myeloid leukemia. Blood. 2016; 127:53-61.
(11) Thomas D, Majeti R. Biology and relevance of human acute myeloid leukemia stem cells. Blood. 2017; 129: 1577-1585.
(12) Shlush L I, Zandi S, Mitchell A et al. Identification of pre-leukaemic haematopoietic stem cells in acute leukaemia. Nature. 2014; 506:328-333.
(13) Wang J C, Dick J E. Cancer stem cells: lessons from leukemia. Trends Cell Biol. 2005; 15:494-501.
(14) Clarke M F, Dick J E, Dirks P B et al. Cancer stem cells—perspectives on current status and future directions: AACR Workshop on cancer stem cells. Cancer Res. 2006; 66:9339-9344.
(15) Jiang X, Saw K M, Eaves A, Eaves C. Instability of BCR-ABL gene in primary and cultured chronic myeloid leukemia stem cells. J Natl Cancer Inst. 2007; 99:680-693.
(16) Jiang X, Zhao Y, Smith C et al. Chronic myeloid leukemia stem cells possess multiple unique features of resistance to BCR-ABL targeted therapies. Leukemia. 2007; 21:926-935.
(17) Kreso A, Dick J E. Evolution of the cancer stem cell model. Cell Stem Cell. 2014; 14:275-291.
(18) Graham D K, DeRyckere D, Davies K D, Earp H S. The TAM family: phosphatidylserine sensing receptor tyrosine kinases gone awry in cancer. Nat Rev Cancer. 2014; 14:769-785.
(19) Schoumacher M, Burbridge M. Key Roles of Axl and MER Receptor Tyrosine Kinases in Resistance to Multiple Anticancer Therapies. Curr Oncol Rep. 2017; 19:19.
(20) Schmidt T, Ben Batalla I, Schultze A, Loges S. Macrophage-tumor crosstalk: role of TAMR tyrosine kinase receptors and of their ligands. Cell Mol Life Sci. 2012; 69:1391-1414.
(21) Janning M, Ben Batalla I, Loges S. Axl inhibition: a potential road to a novel acute myeloid leukemia therapy? Expert Rev Hematol. 2015; 8:135-138.
(22) Rochlitz C, Lohri A, Bacchi M et al. Axl expression is associated with adverse prognosis and with expression of BCL-2 and CD34 in de novo acute myeloid leukemia (AML): results from a multicenter trial of the Swiss Group for Clinical Cancer Research (SAKK). Leukemia. 1999; 13:1352-1358.
(23) Ben Batalla I, Schultze A, Wroblewski M et al. Axl, a prognostic and therapeutic target in acute myeloid leukemia mediates paracrine crosstalk of leukemia cells with bone marrow stroma. Blood. 2013; 122:2443-2452.
(24) Park I K, Mishra A, Chandler J et al. Inhibition of the receptor tyrosine kinase Axl impedes activation of the FLT3 internal tandem duplication in human acute myeloid leukemia: implications for Axl as a potential therapeutic target. Blood. 2013; 121:2064-2073.
(25) Ben Batalla I, Erdmann R, Jorgensen H et al. Axl Blockade by BGB324 Inhibits BCR-ABL Tyrosine Kinase Inhibitor-Sensitive and -Resistant Chronic Myeloid Leukemia. Clin Cancer Res. 2017; 23:2289-2300.
(26) Myers S H, Brunton V G, Unciti-Broceta A. Axl inhibitors in cancer: A medicinal chemistry perspective. J Med Chem. 2016; 59:3593-3608.
(27) Sheridan C. First Axl inhibitor enters clinical trials. Nat Biotechnol. 2013; 31:775-776.

EXAMPLES

The following combination therapy examples are provided by way of illustration, not limitation. In the following combination therapy examples, 3-(5-(cyclopropylmethyl)-1,3,4-oxadiazol-2-yl)-5-(1-(piperidin-4-yl)-1H-pyrazol-4-yl)pyridin-2-amine, which is a compound of Formula (I) and designated in the following examples and FIGS. 1-11 as "Compound A" or "Cmpd A", was assayed for its ability to prevent, treat or manage metastatic cancer, either alone or in combination with a BCL-2 family protein inhibitor.

Example 1

Determination of Combination Index in Cell Based Assay

Cells, Culture Conditions and Reagents:
The AML cell lines Molm-13 and MV4-11 were obtained from DSMZ. The cells were maintained in culture using RPMI-1640 containing 10% heat-inactivated serum at 37° C./5% $CO_2$. For all experiments, unless otherwise specified, the above-mentioned culture conditions were used. The BCL-2 inhibitors venetoclax (ABT-199) and navitoclax (ABT-263) were purchased from Chemietek. The Axl inhibitor 3-(5-(cyclopropylmethyl)-1,3,4-oxadiazol-2-yl)-5-(1-(piperidin-4-yl)-1H-pyrazol-4-yl)pyridin-2-amine (Compound A) was synthesized according to the method disclosed in WO2015/081257.

Compound Dose Response Assays and CompuSyn Analysis:

The AML cells Molm-13 and MV4-11 were plated at $5 \times 10^4$ cells/mL in 24-well plates and dosed the following day using single or combination of drugs with vehicle (DMSO) only controls. Each cell treatment was conducted in duplicates. Cells were collected 48- or 72-hours post drug treatment, mixed 1:1 with trypan blue and counted manually using a hemocytometer. A total of 100 cells (at the least) were counted for each sample. The % viability was calculated and normalized to vehicle treated controls. Individual $IC_{50}$ of each compound was determined in each cell line using increasing doses. Four doses less than the $IC_{50}$ for each compound for each cell line were chosen to conduct the combination studies. The $IC_{50}$ values were calculated using Prism Version 5.01. CompuSyn software Version 1.0 was used to calculate the combination indices.

Results:

To ascertain the potential synergy between BCL-2 inhibitors and Axl inhibitors, the AML cell lines Molm-13 and MV4-11, which are sensitive to BCL-2 inhibitors venetoclax and navitoclax, were chosen for the studies. Both these cell lines have been demonstrated to have low nanomolar $IC_{50}$ for the BCL-2 inhibitors tested. In the venetoclax sensitive cell lines, Molm-13 and MV4-11, the single agent $IC_{50}$ values with venetoclax were found to be 55.91 nM and 20.53 nM respectively. These $IC_{50}$ values were reduced significantly in the presence of Compound A. The $IC_{50}$ values of ABT-199 reduced to 9.9 nM in Molm-13 and to 0.99 nM in MV4-11 when Compound A was present. The $IC_{50}$ values of ABT-263 were determined to be 358.4 nM and 93.47 nM for Molm-13 and MV4-11 respectively. Similar to the situation of ABT-199, the $IC_{50}$ values for ABT-263 also decreased to 116 nM and 36.75 nM in Molm-13 and MV4-11 respectively in the presence of Compound A. These results are summarized in Table 1.

AML samples (with mixed lineage leukemia (MLL) fusions and without MLL fusions) with an Axl-APC antibody was performed. CD34$^+$ AML stem/progenitor cells and stem-enriched CD34$^+$ CD38$^-$ AML populations were included, as the latter has been reported to have high levels of Axl expression in some AML patients.

As FIGS. 2A and 2B demonstrate, AML patient samples express higher levels of Axl on the surface than normal bone marrow (NBM) donor cells. FIG. 2A is a summary of surface staining of Axl with an Axl-APC antibody of CD34+ AML and NBM cells (top) and details for each sample (bottom). FIG. 2B is a summary of surface staining of Axl for stem-enriched CD34+CD38− AML and NBM populations (top) and details for each sample (bottom).

Figure 3A:
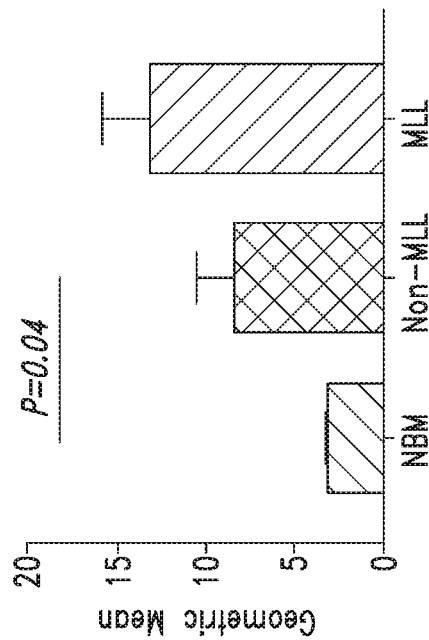
FIGS. 3A and 3B show mean cell surface expression of Axl for AML patient samples and NBM donor cells for CD34+ AML and stem-enriched CD34+CD38− AML respectively.
Figure 3B:
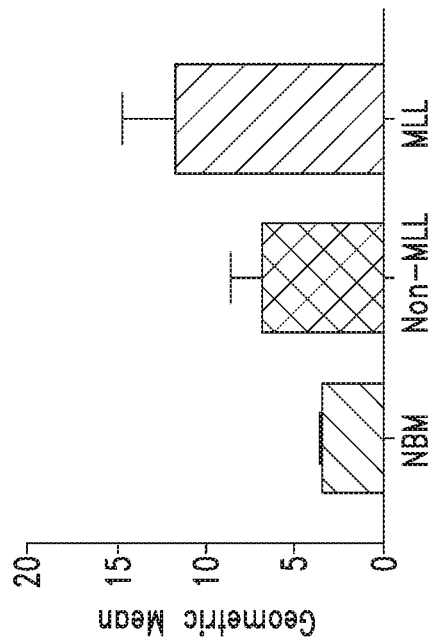

FIGS. 3A and 3B further demonstrate that MLL AML patient samples express high levels of Axl on the surface. FIG. 3A is a summary of surface staining of Axl with an Axl-APC antibody of CD34+ AML and NBM cells. FIG. 3B is a summary of surface staining of Axl for stem-enriched CD34+CD38− AML and NBM populations.

Results:

The results have indicated that Axl protein is expressed on CD34$^+$ AML patient cells at a significantly higher level compared to healthy CD34$^+$ NBM cells (FIG. 2A), with some MLL AML samples expressing the highest Axl levels (FIG. 2A and FIG. 3A). Interestingly, CD34$^+$ CD38$^-$ stem-enriched AML patient samples express slightly higher protein levels of Axl and significantly more Axl than their normal counterparts (FIG. 2B), with MLL AML samples expressing on average higher Axl protein levels (FIG. 3B). AML samples #2 and #14 express high levels of Axl and were used for the PDX model in vivo.

TABLE 1

|  | $IC_{50}$ (nM) | | | | $IC_{50}$ (nM) | | |
| --- | --- | --- | --- | --- | --- | --- | --- |
|  | Cmpd A $IC_{50}$ (nM) | ABT-199 | ABT-199 + Cmpd A | Fold of Shift | ABT-263 | ABT-263 + Cmpd A | Fold of Shift |
| Molm-13 | 429.8 | 55.9 | 9.9 | 5.6 | 358.4 | 116 | 3.1 |
| MV4-11 | 421.2 | 20.5 | 0.99 | 20.7 | 93.5 | 36.8 | 2.5 |

For the combination studies, four concentrations were chosen such that each single compound concentration was lower than that of its single agent $IC_{50}$ in order to establish the synergy of the combination of the compounds evaluated. If the Combination Index (CI) is less than 1, it indicates that the two compounds in combination would have a synergistic effect. FIGS. 1A and 1B show that the combination indices were less than 1 for both cell lines. The results demonstrate that the combinations of Axl inhibitor Compound A with BCL-2 inhibitor ABT-199 or with ABT-263, have both produced synergistic effects in the AML cell lines Molm-13 and MV4-11. The fraction affected (FA) at the same dose was much higher for the compound combination groups compared to that of the single compound groups.

Example 2

AXL Surface Staining

Methods/Experimental Design:

To investigate which AML patient sample expresses high protein levels of Axl, surface staining of various different Example 3

Combination Therapy of Compound A and ABT-199 in a Patient-Derived Xenograft (PDX) Model Methods/Experimental Design:

The relative effectiveness of Compound A and the combination of Compound A and ABT-199 in targeting primitive leukemic cells and/or to prevent leukemia development were investigated in in vivo assays. First, highly purified CD34+ stem and progenitor cells from two different AML patients (with high Axl and GAS6 expression; cohort 1=AML patient #2, cohort 2=AML patient #14, as determined in Example 2) were transduced with a GFP/Luciferase lentivirus reporter to allow non-invasive in vivo imaging (IVIS) of the mice to track leukemia development. Then, an optimized cell number of 50,000 cells per mouse were injected intravenously into the irradiated female immunocompromised NRG-3GS mice (producing human IL-3, GMC-SF and Steel factor), followed by intraperitoneal anti-diphtheria toxin injections on Day 1 and 2 post cell injections to eliminate residual T-cells that could potentially kill the mice. Three weeks later, IVIS was performed to confirm leukemia initiation in all mice. Following that, treatment with vehicle (control), 50 mg/kg Compound A alone QD, 50 mg/kg ABT-199 alone QD or a combination of Compound A (50 mg/kg, QD) and ABT-199 50 mg/kg (QD) was initiated by oral gavage for 4 weeks (total of 20 doses) before another round of IVIS was performed to assess the effectiveness of the treatments.

FIGS. 4A and 4B show the bioluminescent imaging of representative mice before and after oral gavages with indicated treatments, respectively. Darkened areas represent sites of observed bioluminescence resultant from presence of GFP/Luciferase leukemic cells.

Leukemic cell burden was also measured in peripheral blood (PB), bone marrow (BM) and spleens in one set of euthanized mice (one mouse from each treatment group in both cohorts, respectively) and immunophenotypes of engrafted cells determined with fluorescently-labelled CD45, CD34, CD38, CD33, CD15, CD14, CD19 surface markers. Splenomegaly was assessed by spleen sizes and weights (FIG. 5). FIG. 6 shows fluorescence-activated cell sorting (FACS) analysis of engraftment of transduced (GFP+) and untransduced (GFP−) human leukemic cells in PB and BM of representative euthanized mice from each treatment group as indicated for each patient cohort.

Figure 7A:
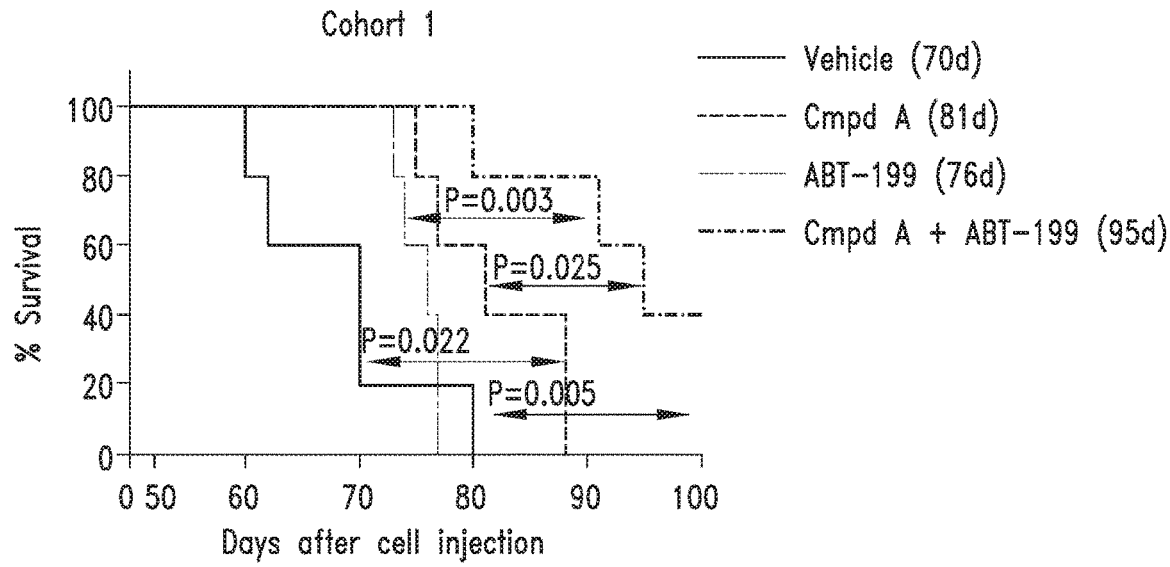
FIG. 7A and FIG. 7B show the survival curves of leukemic mice in a PDX model of AML for treatment groups Cohort 1 and Cohort 2, respectively.
Figure 7B:
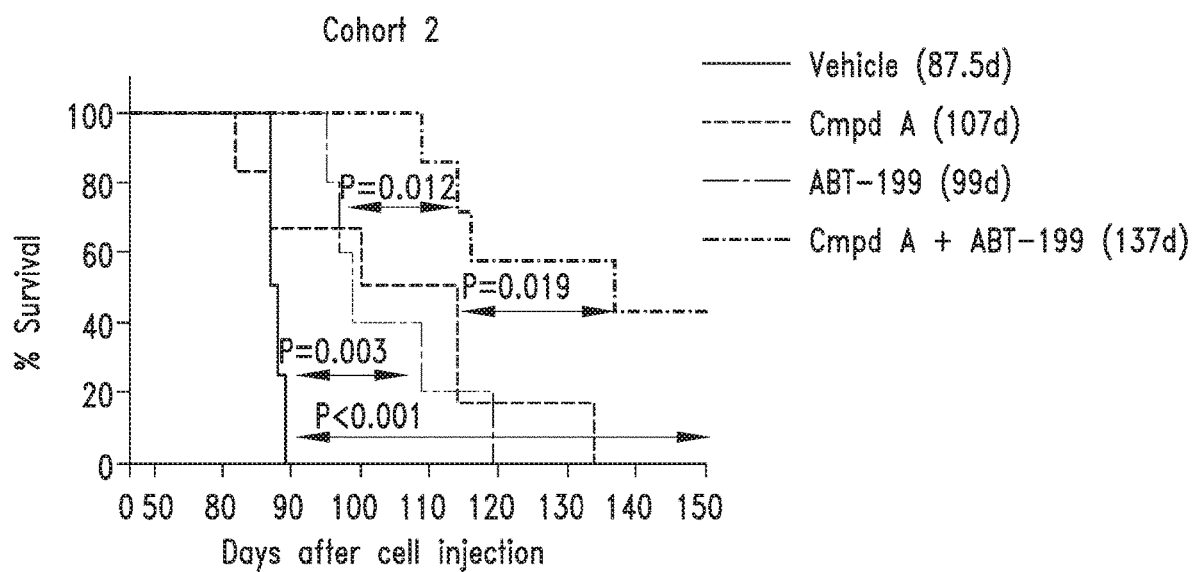

All remaining mice were monitored for symptoms of disease development (weight loss, lethargy etc.) and survival between treatment groups compared. FIGS. 7A and 7B show survival curves of leukemic mice for indicated treatment groups for both patient cohorts. Median survival for each treatment group is indicated in days in brackets. P-values were calculated with the Log-rank (Mantel-Cox) test and significant differences between groups are indicated.

Results:

The combination of Compound A with ABT-199 was highly effective in not only delaying but eliminating leukemia development at early time points, while single agents and especially vehicle controls displayed leukemia progression. See e.g., PDX model of AML pre-treatment (FIG. 4A) and post-treatment (FIG. 4B).

Furthermore, the combination approach to targeting Axl and BCL-2 simultaneously was able to prevent splenomegaly. FIG. 5 shows the sizes and weights of healthy, non-leukemic mice (no cells), vehicle control (no treatment), monotherapy by Compound A alone, ABT-199 alone, and combination therapy by Compound A and ABT-199. As shown, the spleens were significantly enlarged in the vehicle control and monotherapy groups when compared to those of the healthy, non-leukemic mice; whereas the mice undergoing combination therapy showed no sign of spleen enlargement.

FIGS. 6A-6D further demonstrate the reduction of engraftment of human leukemic cells in PB (FIG. 6A and FIG. 6B) and BM (FIG. 6C and FIG. 6D) and infiltration of leukemic cells into the spleen. As a result, significant survival advantage was shown in the combination therapy group as compared to mice treated with single agents or vehicle in both patient cohorts (FIG. 7A and FIG. 7B, $P \leq 0.025$). Detailed analyses of the BM of representative leukemic mice revealed that the concurrent Axl and BCL-2 inhibition was very effective in eliminating engrafted stem cells, progenitors and differentiated blast cells, as well as myeloid cells and myeloid blasts. In conclusion, the combined treatment with Compound A and ABT-199 decreases leukemia burden and enhances survival of leukemic mice significantly in a patient-derived xenograft (PDX) model with primary AML patient cells.

Example 4

Combination Therapy of Compound A and ABT-199 in MV4-11 Cell Line Xenograft Model Methods/Experimental Design:

To investigate the safety and the effectiveness of Compound A monotherapy and combination therapy with ABT-199 for eliminating human leukemic cells in animals, a cell-line based xenograft mouse study was performed. First, MV4-11 cells were transduced with a GFP/Luciferase lentivirus vector to allow sorting/analyzing of human leukemic cells in mice and the non-invasive in vivo imaging system (IVIS) of the mice to track leukemia development and leukemia forming sites. Then, 2.5 million of GFP positive MV4-11 cells per mouse were injected intravenously into irradiated male NRG mice. Two weeks after injection, IVIS imaging was performed to confirm leukemia formation and consistent levels of leukemia burden in each mouse. Following that, mice received 3 weeks (total of 15 doses) of oral treatment with vehicle (control), 50 mg/kg Compound A alone QD, 50 mg/kg ABT-199 alone QD or a combination of Compound A (50 mg/kg, QD) and ABT-199 (50 mg/kg, QD).

Figures 8A, 8B:
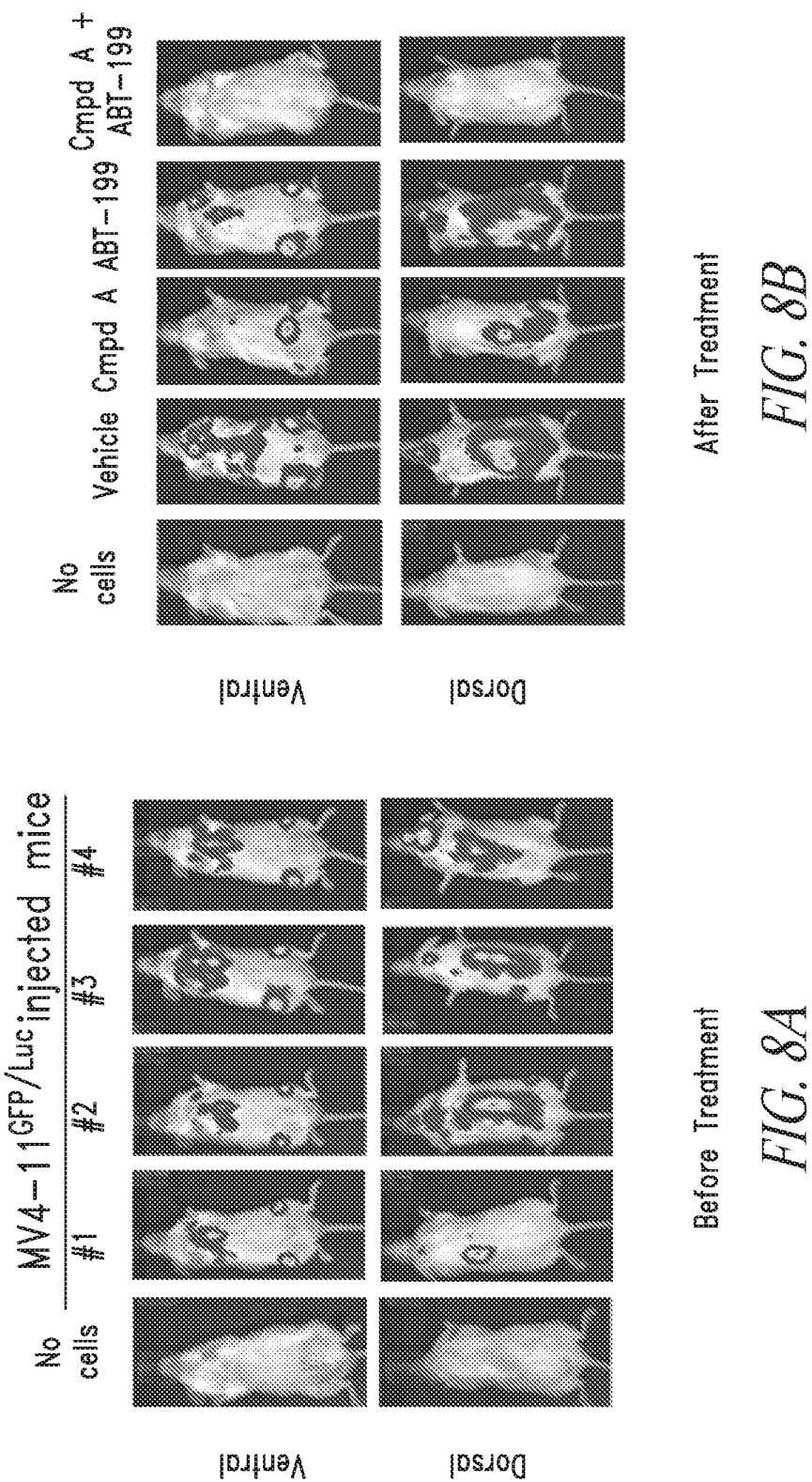
FIGS. 8A and 8B show bioluminescent images of mice in a MV4-11 cell line xenograft model of AML before treatment (FIG. 8A) and after treatment (FIG. 8B) with Axl inhibitor monotherapy, BCL-2 inhibitor monotherapy and Axl/BCL-2 combination therapy.

After the treatment period, another round of IVIS imaging was performed to evaluate the effectiveness of the treatments. FIG. 8A and FIG. 8B show the bioluminescent imaging of representative mice before treatment and after oral gavages with indicated treatments, respectively. Darkened areas represent sites of observed bioluminescence resultant from presence of GFP/Luciferase leukemic cells. For comparison, healthy mice with no transduced leukemic cells ("no cells") are also shown.

Figure 9A:
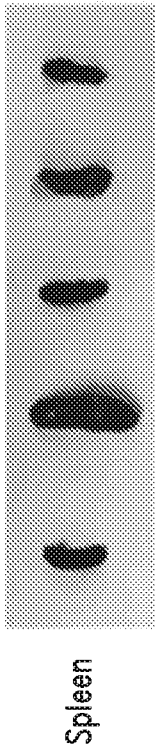
FIG. 9A shows spleen sizes and weights of representative euthanized mice in a MV4-11 cell line xenograft model of AML from each treatment group as indicated.
Figure 9B:
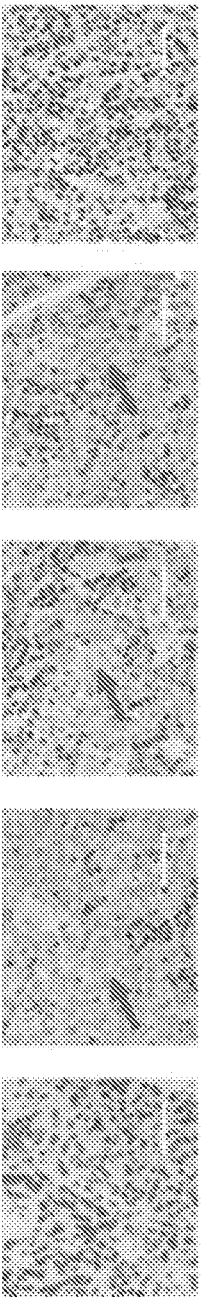
FIG. 9B shows Haemotoxylin and Eosin staining of representative euthanized mice in a MV4-11 cell line xenograft model of AML from each treatment group as indicated.
Figure 10:
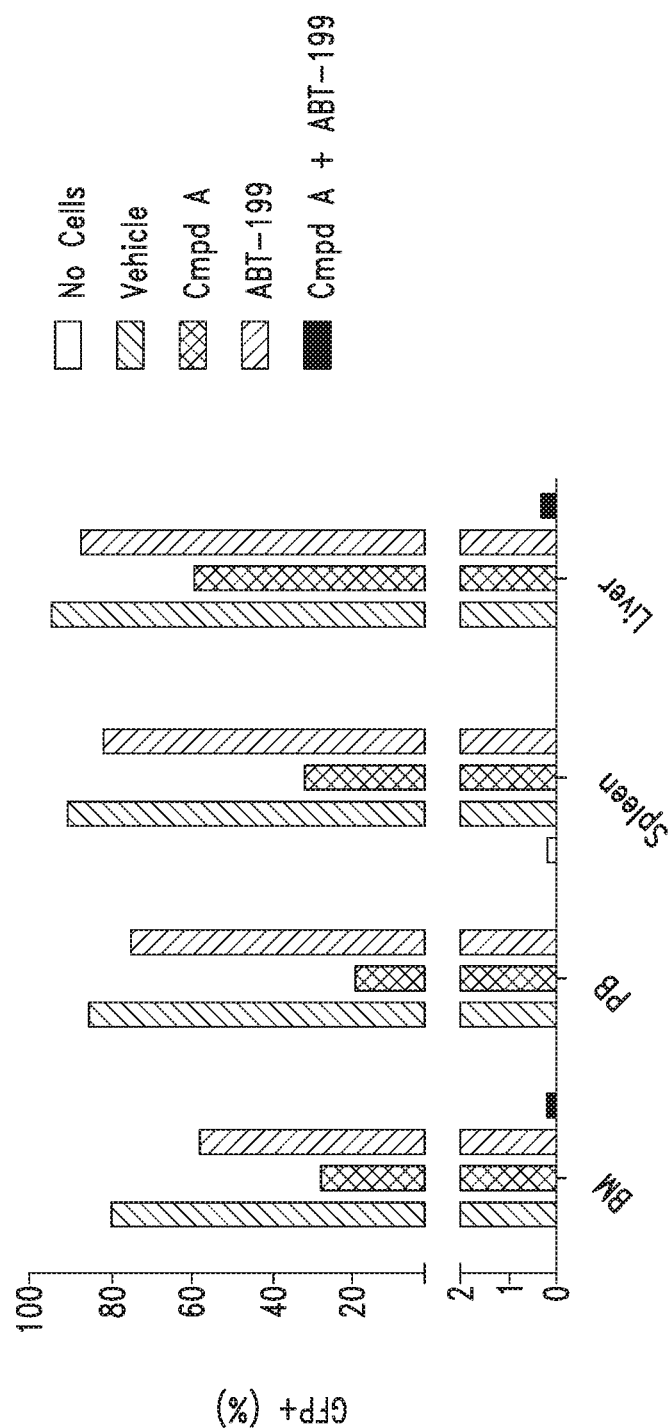
FIG. 10 shows FACS analysis of leukemic cell engraftment in PB, BM, spleen and liver of representative mice in a MV4-11 cell line xenograft model of AML from each treatment group as indicated.

A representative group of mice was then sacrificed to compare engraftment of leukemic cells in peripheral blood (PB), bone marrow (BM), spleens and livers of each treatment group. Infiltration of leukemic cells into hematopoietic organs as spleen and liver was assessed by weights and histopathologic analysis. FIGS. 9A and 9B show spleen sizes and weights, and Haemotoxylin and Eosin staining of representative mice from each treatment group as indicated, respectively. FIG. 10 shows FACS analysis of leukemic cell engraftment in BM, PB, spleen and liver of representative mice from each treatment group as indicated.

Figure 11:
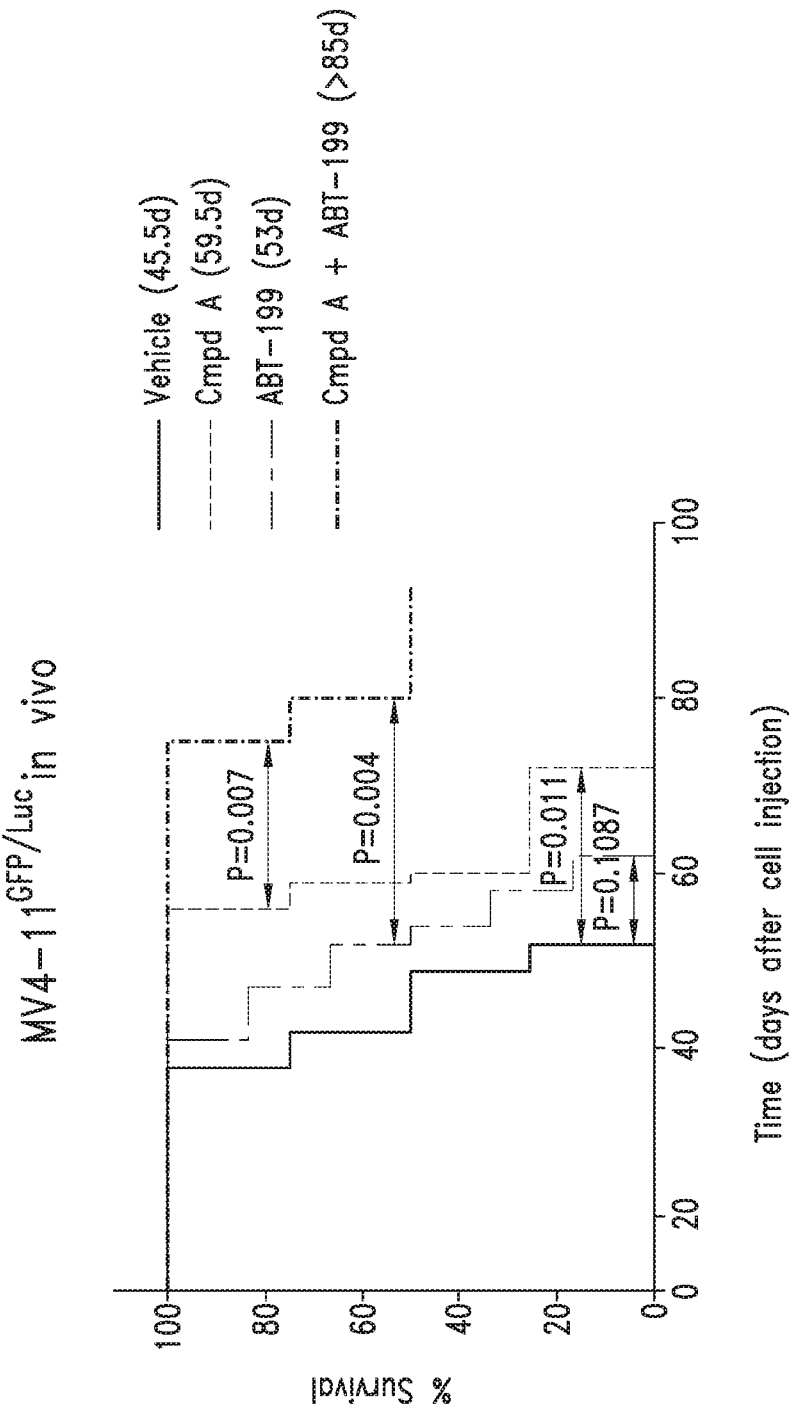
FIG. 11 shows survival curves of leukemic mice in a MV4-11 cell line xenograft model of AML for indicated treatment groups.

The remaining mice were monitored for survival between treatment groups. FIG. 11 shows survival curves of leukemic mice for indicated treatment groups. Median survival for each treatment group is indicated in days in brackets. P-values were calculated with the Log-rank (Mantel-Cox) test and significant differences between groups are indicated.

Results:

After three weeks of oral gavage, Compound A treated mouse had dramatically lower intensity bioluminescent signals compared to vehicle and ABT-199 treated mice and the signal of combination treated mouse was even below detection threshold (FIG. 8B). This observation was corroborated further by no sign of spleen enlargement in mice treated with Compound A or in combination with ABT-199 as compared to vehicle control and ABT-199 treated mice (FIG. 9A). Histological analysis further confirmed that the combination treatment had prevented infiltration of leukemic cells in the spleen (FIG. 9B). Fluorescence-activated cell sorting (FACS) analysis showed combination therapy reduced the engraftment of human leukemic cells in PB, BM, spleen and liver (FIG. 10), resulting in a significant prolonged survival compared to mice treated with single agents or vehicle (FIG.

11, P<0.007). In summary, Compound A treatment alone can reduce leukemia propagating activity in vivo in this MV4-11 animal model and this inhibitory effect has been dramatically enhanced after combination treatment with ABT-199.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

What is claimed is:

1. A method for treating blood cancer in a subject in need thereof, the method comprising administering to the subject a combination of an Axl inhibitor and a B-cell leukemia/lymphoma 2 (BCL-2) family protein inhibitor, wherein;
the Axl inhibitor is 3-(5-(cyclopropylmethyl)-1,3,4-oxadiazol-2-yl)-5-(1-(piperidin-4-yl)-1H-pyrazol-4-yl)pyridin-2-amine, a stereoisomer thereof, an enantiomer thereof, a tautomer thereof, a pharmaceutically acceptable salt thereof and/or a pharmaceutical composition thereof; and
the BCL-2 family protein inhibitor is at least one of:

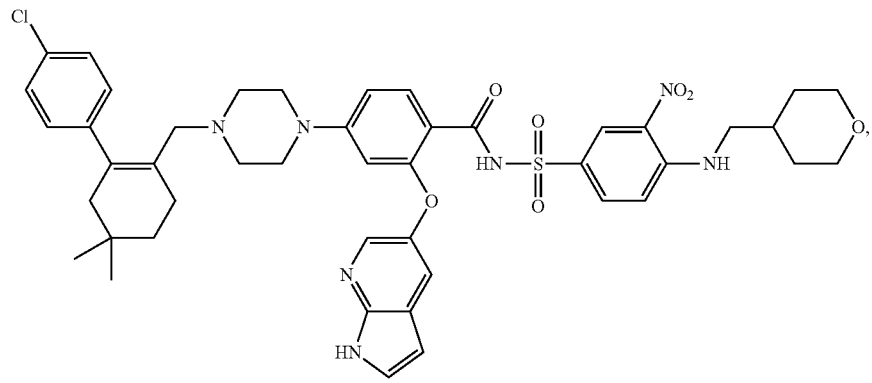

(Venetoclax)

a stereoisomer thereof, an enantiomer thereof, a tautomer thereof, a pharmaceutically acceptable salt thereof and/or a pharmaceutical composition thereof, or a stereoisomer thereof, an enantiomer thereof, a tautomer thereof, a pharmaceutically acceptable salt thereof and/or a pharmaceutical composition thereof.

2. The method of claim 1, wherein the Axl inhibitor is the 3-(5-(cyclopropylmethyl)-1,3,4-oxadiazol-2-yl)-5-(1-(piperidin-4-yl)-1H-pyrazol-4-yl)pyridin-2-amine; and the BCL-2 family protein inhibitor is the Venetoclax.

3. The method of claim 1, wherein the Axl inhibitor is the 3-(5-(cyclopropylmethyl)-1,3,4-oxadiazol-2-yl)-5-(1-(piperidin-4-yl)-1H-pyrazol-4-yl)pyridin-2-amine; and the BCL-2 family protein inhibitor is the Navitoclax.

4. The method of claim 1, wherein the blood cancer is acute myeloid leukemia (AML).

5. The method of claim 1, wherein the Axl inhibitor is administered at a lower dose than a monotherapy using the Axl inhibitor.

6. The method of claim 1, wherein the BCL-2 family protein inhibitor is administered at a lower dose than a monotherapy using the BCL-2 family protein inhibitor.

7. The method of claim 2, wherein the blood cancer is acute myeloid leukemia (AML).

8. The method of claim 2, wherein the Axl inhibitor is administered at a lower dose than a monotherapy using the Axl inhibitor.

9. The method of claim 2, wherein the BCL-2 family protein inhibitor is administered at a lower dose than a monotherapy using the BCL-2 family protein inhibitor.

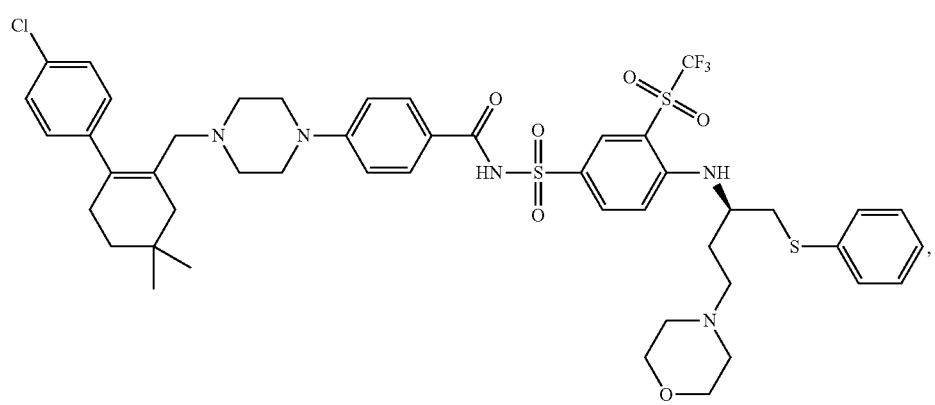

(Navitoclax)

10. The method of claim 3, wherein the blood cancer is acute myeloid leukemia (AML).

11. The method of claim 3, wherein the Axl inhibitor is administered at a lower dose than a monotherapy using the Axl inhibitor.

12. The method of claim 3, wherein the BCL-2 family protein inhibitor is administered at a lower dose than a monotherapy using the BCL-2 family protein inhibitor.

* * * * *